United States Patent
Terrett

(10) Patent No.: US 7,745,156 B2
(45) Date of Patent: Jun. 29, 2010

(54) METHODS FOR DIAGNOSIS AND TREATMENT OF EPITHELIAL-DERIVED CANCERS

(75) Inventor: Jonathan Alexander Terrett, Slough (GB)

(73) Assignee: UCB Pharma S.A., Brussels (BE)

( * ) Notice: Subject to any disclaimer, the term of this patent is extended or adjusted under 35 U.S.C. 154(b) by 94 days.

(21) Appl. No.: 11/880,650

(22) Filed: Jul. 23, 2007

(65) Prior Publication Data
US 2009/0148439 A1 Jun. 11, 2009

Related U.S. Application Data

(60) Division of application No. 10/981,381, filed on Nov. 4, 2004, now Pat. No. 7,261,892, which is a continuation-in-part of application No. 10/496,892, filed as application No. PCT/GB02/05335 on Nov. 27, 2002, now abandoned.

(60) Provisional application No. 60/333,436, filed on Nov. 27, 2001.

(51) Int. Cl.
G01N 33/53 (2006.01)
(52) U.S. Cl. ........................ 435/7.23; 435/7.1; 435/7.9; 435/7.92; 436/532
(58) Field of Classification Search ................ None
See application file for complete search history.

(56) References Cited

FOREIGN PATENT DOCUMENTS

WO 94/05691 * 3/1994

OTHER PUBLICATIONS

Agematsu et al., Eur. J. Immunol., 25:2825-2829 (1995).
Bowman et al., J. Immunol., 152:1756-1761 (1994).
Brown et al., J. Immunol., 154:3686-3695 (1995).
Bui et al., Clinical Cancer Res., 9:802-811 (2003).
Divgi et al., Clinical Cancer Res., 4:2729-2739 (1998).
Flanigan et al., Current Treatment Options in Oncology, 4:385-390 (2003).
Held-Feindt et al., Int. J. Cancer; 98:352-356 (2002).
Hintzen et al., J. Immunol., 154:2612-2623 (1995).
Kammula et al., Cancer, 83:797-805 (1998).
Kennett et al., Current Opinion in Molecular Therapeutics, 5:70-75 (2003).
Kobata et al., Proc. Natl. Acad. Sci. U.S.A., 92:11249-11253 (1995).
Krown, Cancer, 59:647-651 (1987).
Lens et al., Leukemia and Lymphoma, 18:51-59 (1995).
Li et al., Clinical Cancer Res., 7:89-92 (2001).
Motzer et al., Journal of Clinical Oncology, 17:2530-2540 (1999).
Muss, Seminars in Oncology, 15:30-34 (1988).
Oosterwijk et al., Proc. Amer. Assoc. Cancer Res., 37:461 (1996).
Pastorek et al., Oncogene, 9:2877-2888 (1994).
Prasad et al., Proc. Natl. Acad. Sci. U.S.A., 94:6346-6351 (1997).
Ranheim et al., Blood, 85:3556-3565 (1995).
Steffens et al., Clinical Cancer Res., 5:3268-3274 (1999; Suppl.).
Uemura et al., British Journal of Cancer, 81:741-746 (1999).
van Herpen et al., British Journal of Cancer, 82:772-776 (2000).
Yagoda et al., Seminars in Oncology, 22:42-60 (1995).
Yang et al., Immunology, 88:289-293 (1996).

* cited by examiner

*Primary Examiner*—Sheela J Huff
(74) *Attorney, Agent, or Firm*—Klauber & Jackson LLC

(57) ABSTRACT

The present invention relates to the use of a polypeptide (CD27L) for diagnosis of epithelial-related cancers, in particular kidney cancer e.g. renal cell cancer and colorectal cancer, e.g. colon cancers, as well as in methods of treatment of such cancers.

17 Claims, 7 Drawing Sheets

Figure 1

```
                                                                              60
ccagagaggggcaggcttgtcccctgacaggttgaagcaagtagacgcccaggagccccg
                                                                             120
ggaggggggctgcagtttccttccttccttctcggcagcgctccgcgcccccatcgccct M  P  E  G  S  G  C  S  V                  10
cctgcgctagcggaggtgatcgccgcggcgatgccggaggagggttcgggctgctcggtg                 180

R  R  R  P  Y  G  C  V  L  R  A  A  L  V  P  L  V  A  G  L                  30
cggcgcaggccctatgggtgcgtcctgcgggctgctttggtcccattggtcgcgggcttg                 240

V  I  C  L  V  V  C  I  Q  R  F  A  Q  A  Q  Q  Q  L  P  L                  50
gtgatctgcctcgtggtgtgcatccagcgcttcgcacaggctcagcagcagctgccgctc                 300

E  S  L  G  W  D  V  A  E  L  Q  N  H  T  G  P  Q  Q  D                     70
gagtcacttgggtgggacgtagctgagctgcagctgaatcacacaggacctcagcaggac                 360

P  R  L  Y  W  Q  G  G  P  A  L  G  R  S  F  L  H  G  P  E                  90
cccaggctatactggcaggggggcccagcactgggccgctccttcctgcatggaccagag                 420

L  D  K  G  Q  L  R  I  H  R  D  G  I  Y  M  V  H  I  Q  V                 110
ctggacaaggggcagctacgtatccatcgtgatggcatctacatggtacacatccaggtg                 480

T  L  A  I  C  S  S  T  T  A  S  R  H  H  P  T  T  L  A  V                 130
acgctggccatctgctcctccacgacggcctccaggcaccaccccaccaccctggccgtg                 540

G  I  C  S  P  A  S  R  S  I  S  L  L  R  L  S  F  H  Q  G                 150
ggaatctgctctcccgcctcccgtagcatcagcctgctgcgtctcagcttccaccaaggt                 600

C  T  I  V  S  Q  R  L  T  P  L  A  R  G  D  T  L  C  T  N                 170
tgtaccattgtctcccagcgcctgacgcccctggcccgaggggacacactctgcaccaac                 660

L  T  G  T  L  L  P  S  R  N  T  D  E  T  F  F  G  V  Q  W                 190
ctcactgggacacttttgccttcccgaaacactgatgagaccttctttggagtgcagtgg                 720

V  R  P  *                                                                  193
gtgcgcccctgaccactgctgctgattagggttttttaaattttatttttatttta                     780
gttcaagagaaaaagtgtacacacaggggccacccgggggttggggtgggagtgtggtggg                840
gggtagtttgtggcaggacaagagaaggcattgagcttttttctttcattttcctattaaa                900
aaatacaaaaatcaaaacaaaaaaaa                                                   926
```

SEQUENCE LISTING

<160> NUMBER OF SEQ ID NOS: 4

<210> SEQ ID NO 1
<211> LENGTH: 926
<212> TYPE: DNA
<213> ORGANISM: Homo sapiens

<400> SEQUENCE: 1

```
ccagagaggg gcaggcttgt cccctgacag gttgaagcaa gtagacgccc aggagcccg      60 ggaggggct gcagtttcct tccttccttc tcggcagcgc tccgcgcccc catcgcccct     120
cctgcgctag cggaggtgat cgccgcggcg atgccggagg agggttcggg ctgctcggtg     180
```

-continued

```
cggcgcaggc cctatgggtg cgtcctgcgg gctgctttgg tcccattggt cgcgggcttg    240
gtgatctgcc tcgtggtgtg catccagcgc ttcgcacagg ctcagcagca gctgccgctc    300
gagtcacttg ggtgggacgt agctgagctg cagctgaatc acacaggacc tcagcaggac    360
cccaggctat actggcaggg gggcccagca ctggccgct ccttcctgca tggaccagag     420
ctggacaagg ggcagctacg tatccatcgt gatggcatct acatggtaca catccaggtg    480
acgctggcca tctgctcctc cacgacggcc tccaggcacc accccaccac cctggccgtg    540
ggaatctgct ctcccgcctc ccgtagcatc agcctgctgc gtctcagctt ccaccaaggt    600
tgtaccattg tctcccagcg cctgacgccc tggcccgag gggacacact ctgcaccaac     660
ctcactggga cacttttgcc ttcccgaaac actgatgaga ccttctttgg agtgcagtgg    720
gtgcgcccct gaccactgct gctgattagg gttttttaaa ttttatttta ttttatttaa    780
gttcaagaga aaaagtgtac acacaggggc cacccggggt tggggtggga gtgtggtggg    840
gggtagtttg tggcaggaca agagaaggca ttgagctttt tctttcattt tcctattaaa    900
aaatacaaaa atcaaaacaa aaaaaa                                         926
```

<210> SEQ ID NO 2
<211> LENGTH: 193
<212> TYPE: PRT
<213> ORGANISM: Homo sapiens

<400> SEQUENCE: 2

```
Met Pro Glu Glu Gly Ser Gly Cys Ser Val Arg Arg Arg Pro Tyr Gly
 1               5                  10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
 65                 70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Val Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

<210> SEQ ID NO 3
<211> LENGTH: 22
<212> TYPE: DNA
<213> ORGANISM: Artificial Sequence
<220> FEATURE:
<223> OTHER INFORMATION: primer

```
<400> SEQUENCE: 3
gctgctttgg tcccattggt cg                                      22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
gaggtcctgt gtgattcagc tg                                      22
```

US 7,745,156 B2

METHODS FOR DIAGNOSIS AND TREATMENT OF EPITHELIAL-DERIVED CANCERS

CROSS REFERENCE TO RELATED APPLICATIONS

The present application is a divisional application of application Ser. No. 10/981,381 filed Nov. 4, 2004 (now U.S. Pat. No. 7,261,892, issued Aug. 28, 2007), which is a continuation-in-part of application Ser. No. 10/496,892 filed May 25, 2004, now abandoned which is a National Stage Application claiming the priority of PCT Application No. PCT/GB02/05335 filed Nov. 27, 2002, which in turn, claims priority from U.S. Application Ser. No. 60/333,436, filed Nov. 27, 2001. Applicants claim the benefits of 35 U.S.C. §120 as to U.S. application Ser. Nos. 10/981,381 and 10/496,892 and the PCT application and priority under 35 U.S.C. §119 as to the said United States provisional application, and the entire disclosures of each of these applications are incorporated herein by reference in their entireties.

BACKGROUND OF THE INVENTION

Field of the Invention

The present invention relates to the use of a polypeptide (CD27L) for diagnosis of epithelial-related cancers, in particular kidney cancer e.g. renal cell cancer and colorectal cancer, e.g. colon cancers, as well as in methods of treatment of such cancers. Several publications and patent documents are referenced in this application in order to more fully describe the state of the art to which this invention pertains. The disclosure of each of these publications and documents is incorporated by reference herein in its entirety.

Treatment of most cancer types is usually via surgery, chemotherapy, radiotherapy or biological therapy. However, some tumours become refractory to such treatments, as the cancer cells develop resistance to chemotherapy drugs or lose their hormone sensitivity, leading to recurrent or metastatic disease which is often incurable. More recently, attention has focused on the development of immunological therapies (Green et al. (2000) Cancer Treat. Rev. 26, 269-286; Davis (2000) Immunol. Cell Biol. 78, 179-195; Knuth et al. (2000) Cancer Chemother Pharmacol. 46, S46-51; Shiku et al. (2000) Cancer Chemother. Pharmacol. 46, S77-82; Saffran et al. (1999) Cancer Metastasis Rev. 18, 437-449), such as cancer vaccines and monoclonal antibodies (mAbs), as a means of initiating and targeting a host immune response against tumour cells. In 1998, the FDA approved the use of herceptin (Stebbing et al. (2000) Cancer Treat. Rev. 26, 287-290; Dillman (1999) Cancer Biother. Radiopharm. 14, 5-10; Miller et al: (1999) Invest. New Drugs 17, 417-427), a mAb that recognises the erbB2/HER2-neu receptor protein, as a treatment for metastatic breast cancer. In combination with chemotherapy, herceptin has been shown to prolong the time to disease progression, when compared to patients receiving chemotherapy alone (Baselga et al. (1998) Cancer Res. 58, 2825-2831). The identification of other suitable targets or antigens for immunotherapy of other cancers, for example epithelial-derived cancers, has become increasingly important.

Kidney Cancer

There are three main types of kidney cancer—renal cell cancer that develops in the lining of the renal tubules which filter blood, Wilm's Tumor, found mainly in children under 5 years, and transitional cell cancer of the renal pelvis and/or ureter, that develops in the lining of the bladder, ureters or renal pelvis. Respectively they account for approximately 80%, 5% and 7% of all kidney cancer cases.

As kidney cancer grows, it may invade organs near the kidney, such as the liver, colon, or pancreas. When kidney cancer spreads, cancer cells may appear in the lymph nodes. For this reason, lymph nodes near the kidney may be removed during surgery. Kidney cancer may spread and form new cancers, most often in the bones or lungs.

Surgery is the main treatment for kidney cancer. The aim of surgery is to remove all or as much of the cancer as is possible and to 'stage' the cancer accurately so that the need for any further treatment can be assessed. In radical nephrectomy, the whole kidney along with the cancer is removed. The adrenal gland, which is attached to the kidney, is also removed along with the fatty tissue surrounding the kidney. Nearby lymph nodes are also removed as this helps the doctors decide which stage the cancer is. In a partial nephrectomy, only the part of the kidney that contains the cancer is removed and is less commonly performed. In some circumstances, removal of secondary metastases may be done to relieve symptoms such as pain. However, it does not usually help in terms of prognosis and will only be attempted if the cancer is easy to get to and surgery can be performed without causing any serious side effects. Arterial embolisation is a procedure done to block the artery of the kidney containing the cancer. This procedure may be done to control a primary tumour which surgery cannot remove or occasionally prior to an operation to make surgery easier.

Radiotherapy is sometimes used instead of surgery for patients who are too ill to undergo a major operation. In some circumstances it may be used to help with symptoms that arise as a result of recurrent or advanced cancers. However, renal cell kidney cancers are not particularly sensitive to radiotherapy and its use is not routine because studies have not shown that it improves prognosis.

Immunotherapeutic treatment most commonly uses cytokines interleukin-2 and interferon-alpha for the treatment of advanced (metastatic) kidney cancer.

Colorectal Cancer

Excluding skin cancers, colorectal cancer is the third most common cancer diagnosed in men and women in the United States. Surgery is the main treatment for colorectal cancer. Radiation therapy is often used after surgery to kill unremoved deposits and to prevent local recurrences. Adjuvant chemotherapy may also be used, with drugs such as Fluorouracil (5-FU), optionally with leucovorin or levamisole, and Irinotecan (CPT-11). There are no generally approved immunotherapeutic drugs for the treatment of colorectal cancer, despite the fact that immunotherapy may offer the greatest potential after surgical resection in the adjuvant setting. Edrecolomab (monoclonal antibody 17-1A, or Panorex), however, is an adjunctive therapy for colorectal cancer which is in clinical trials in the UK and the US, and which has already been approved in Germany. Identification of new suitable targets or antigens for immunotherapy of colorectal cancer is therefore highly important.

BRIEF SUMMARY OF THE INVENTION

The present invention is based on the finding that the protein, CD27L, exhibits elevated expression in epithelial-derived cancers, especially kidney cancer and colorectal cancer. The elevated expression of CD27L is useful diagnostically as well as a target for therapeutic treatment. CD27L is a ligand that binds the cytokine CD27 receptor found on the surface of human T and B lymphocytes (U.S. Pat. Nos. 5,573,924; 5,716,805; WO 94/05691; Goodwin et al. (1993) Cell 73(3): 447-456). It was originally identified as CD70 see Hintzen et al Int Immunol, (1994), 6(3), pp 477-80. A study published in 1991 used monoclonal antibodies to various activation antigens including CD70/CD27L and identified that CD70/CD27L had a high expression on activated B and T cells (Paloczi K et al., (1991), Heamatologica, 24(2), pp 83-90). To avoid confusion the protein will be referred to herein as CD27L.

The present invention provides a method of screening for and/or diagnosis of epithelial-derived cancer, in a subject, which method comprises the step of detecting and/or quantifying in a biological sample obtained from said subject, a CD27L polypeptide which:

(a) comprises or consists of the amino acid sequence shown in FIG. 1 (SEQ ID NO:2);
(b) is a derivative having one or more amino acid substitutions, modifications, deletions or insertions relative to the amino acid sequence shown in FIG. 1 (SEQ ID NO: 2) which retains CD27 binding ability; or
(c) is a fragment of a polypeptide having the amino acid sequence shown in FIG. 1 (SEQ ID NO: 2), which is at least ten amino acids long and has at least 70% homology over the length of the fragment.

In a further embodiment, the level of the CD27L polypeptide is compared to a reference range or control.

The polypeptides described in (a) to (c) above are hereinafter referred to as "CD27L polypeptides". The term "polypeptides" includes peptides, polypeptides and proteins. These are used interchangeably unless otherwise specified.

In a further aspect, the present invention provides methods of screening for and/or, diagnosis of epithelial-derived cancer, in a subject, which method comprises the step of detecting and/or quantifying in a biological sample obtained from said subject, a CD27L nucleic acid molecule which:

(d) comprises or consists of the DNA sequence shown in FIG. 1 (SEQ ID NO: 1) or its RNA equivalent;
(e) has a sequence which is complementary to the sequences of (d);
(f) has a sequence which codes for a polypeptide as defined in (a) to (c) above;
(g) has a sequence which shows substantial identity with any of those of (d), (e) and (f); or
(h) is a fragment of (d), (e), (f) or (g), which is at least 8 nucleotides in length.

The nucleic acid molecules described in (d) to (h) above are hereinafter referred to as "CD27L nucleic acids".

In one embodiment, the epithelial-derived cancer is kidney cancer; in a specific embodiment the kidney cancer is renal cell cancer. In another embodiment, the epithelial-derived cancer is colorectal cancer, in a specific embodiment the colorectal cancer is colon cancer. The term "epithelial-derived cancer", as used herein, is intended to encompass both kidney cancer, e.g. renal cell cancer and colorectal cancer, e.g. colon cancer. The subject may be a mammal and is preferably a human.

In another aspect, the present invention provides a method for the prophylaxis and/or treatment of epithelial-derived cancer in a subject, which comprises administering to a subject in need, a therapeutically effective amount of at least one CD27L polypeptide.

In further aspect, the present invention provides a method for the prophylaxis and/or treatment of epithelial-derived cancer in a subject, which comprises administering to a subject in need thereof, a therapeutically effective amount of an agent which modulates the expression or activity of a CD27L polypeptide or modulates the expression of a CD27L nucleic acid. An agent capable of modulating (e.g., increasing or decreasing) CD27L polypeptide expression and/or activity may, for example, be a CD27L antibody. An exemplary antibody capable of decreasing CD27L expression and activity is described herein. See Example 6.

In another aspect, the present invention provides a pharmaceutical composition comprising an agent which modulates the expression or activity of a CD27L polypeptide or modulates the expression of a CD27L nucleic acid for use in the prophylaxis and/or treatment of an epithelial-derived cancer.

In a further aspect, the present invention provides a pharmaceutical composition comprising at least one CD27L polypeptide for use in the prophylaxis and/or treatment of an epithelial-derived cancer.

In the aspects above, the polypeptides or fragments thereof may be provided in isolated or recombinant form, and may be fused to other moieties. The polypeptides or fragments thereof may be provided in substantially pure form, that is to say free, to a substantial extent, from other proteins. Thus, a polypeptide may be provided in a composition in which it is the predominant component present (i.e. it is present at a level of at least 50%; preferably at least 75%, at least 80%, at least 85%, at least 90%, at least 95% or at least 98%; when determined on a weight/weight basis excluding solvents or carriers).

In further aspects of the invention, the CD27L polypeptides, encoding nucleic acids, derivatives and fragments thereof, antibodies thereto, and agonists and antagonists thereof, may be used as part of diagnostic assays including screening assays, to identify the presence or instances of e.g. an epithelial-derived cancer in a patient, as well as to identify other agents that may serve in like capacity, as either diagnostic or possibly therapeutic agents for the treatment of such diseases, all as more fully described and illustrated herein. The method of the invention includes methods for screening of agents capable of modulating the expression or activity of CD27L polypeptides, that is, agents that increase or decrease the expression of the CD27L polypeptide. Further encompassed by the invention are methods for monitoring epithelial-derived cancer treatment in a patient, comprising the step of quantifying the expression or activity of CD27L in a patient undergoing treatment for an epithelial-derived cancer.

Accordingly, the present invention will be better understood from a consideration of the ensuing detailed description which proceeds with reference to the following drawing figures.

BRIEF DESCRIPTION OF THE FIGURES

FIG. 1: shows the nucleotide (SEQ ID NO:1) and amino acid (SEQ ID NO:2) sequences of CD27L. The tandem mass spectra are in bold and underlined.

DETAILED DESCRIPTION

Figure 2:
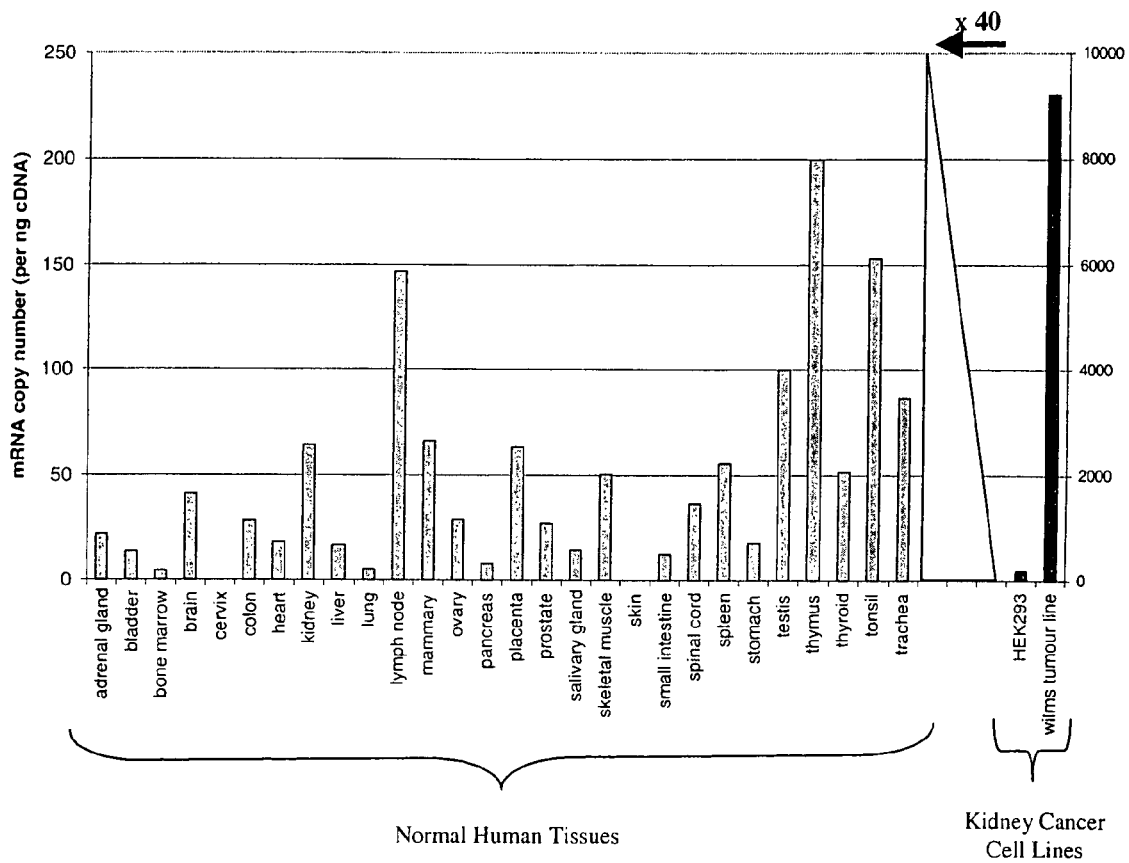
FIG. 2: shows tissue distribution of CD27L mRNA. Levels of mRNA in normal tissues and renal carcinoma cell lines were quantified by real time RT-PCR. mRNA levels are expressed as the number of copies $ng^{-1}$ cDNA.

In order to more fully appreciate the present invention, polypeptides within the scope of (a)-(c) above will now be discussed in greater detail.

Polypeptides within the Scope of (a):

A polypeptide within the scope of (a), may consist of the particular amino acid sequence given in FIG. 1 (SEQ ID NO:2) or may have an additional N-terminal and/or an additional C-terminal amino acid sequence relative to the sequence given in FIG. 1 (SEQ ID NO:2). Additional N-terminal or C-terminal sequences may be provided for various reasons. Techniques for providing such additional sequences are well known in the art. Additional sequences may be provided in order to alter the characteristics of a particular polypeptide. This can be useful in improving expression or regulation of expression in particular expression systems. For example, an additional sequence may provide some protection against proteolytic cleavage. This has been done for the hormone Somatostatin by fusing it at its N-terminus to part of the β galactosidase enzyme (Itakwa et al. (1977) Science 198: 105-63).

Additional sequences can also be useful in altering the properties of a polypeptide to aid in identification or purification. For example, a fusion protein may be provided in which a polypeptide is linked to a moiety capable of being isolated by affinity chromatography. The moiety may be an antigen or an epitope and the affinity column may comprise immobilised antibodies or immobilised antibody fragments which bind to said antigen or epitope (desirably with a high degree of specificity). The fusion protein can usually be eluted from the column by addition of an appropriate buffer. Additional N-terminal or C-terminal sequences may, however, be present simply as a result of a particular technique used to obtain a polypeptide of the present invention and need not provide any particular advantageous characteristic to the polypeptide of the present invention. Such polypeptides are within the scope of the present invention.

Whatever additional N-terminal or C-terminal sequence is present, it is preferred that the resultant polypeptide should exhibit the binding ability of a CD27L polypeptide as shown in FIG. 1 (SEQ ID NO:2).

Polypeptides within the Scope of (b).

Turning now to the polypeptides defined in (b) above, it will be appreciated by the person skilled in the art that these polypeptides are derivatives of the polypeptide given in a) above, provided that such derivatives exhibit the binding ability of the polypeptide having the amino acid sequence shown in FIG. 1 (SEQ ID NO:2). Alterations in the amino acid sequence of a protein can occur which do not affect the function of a protein. These include amino acid deletions, modifications, insertions and substitutions and can result from alternative splicing and/or the presence of multiple translation start sites and stop sites. Polymorphisms may arise as a result of the infidelity of the translation process. Thus changes in amino acid sequence may be tolerated which do not affect the protein's function. The skilled person will appreciate that various changes can often be made to the amino acid sequence of a polypeptide which has a particular activity to produce derivatives (sometimes known as variants or "muteins") having at least a proportion of said activity, and preferably having a substantial proportion of said activity. Such derivatives of the polypeptides described in (a) above may be utilised in the present invention and are discussed in greater detail below. They include allelic and non-allelic derivatives. An example of a derivative of the present invention is a polypeptide as defined in (a) above, apart from the substitution of one or more amino acids with one or more other amino acids. The skilled person is aware that various amino acids have similar properties. One or more such amino acids of a polypeptide can often be substituted by one or more other such amino acids without eliminating a desired activity of that polypeptide.

In one embodiment, the substituted amino acid(s) renders dominant negative activity upon the peptide. In another embodiment, the substituted amino acid(s) renders the polypeptide constitutively active.

Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Substitutions of this nature are often referred to as "conservative" or "semi-conservative" amino acid substitutions.

Amino acid deletions or insertions may also be made relative to the amino acid sequence given in (a) above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence given in (a) above can also be made. This may be done to alter the properties of a CD27L polypeptide (e.g. to assist in identification, purification or expression, as explained above in relation to fusion proteins).

Amino acid changes relative to the sequence given in (a) above can be made using any suitable technique e.g. by using site-directed mutagenesis (Hutchinson et al. (1978) J. Biol. Chem. 253:6551).

It should be appreciated that amino acid substitutions or insertions within the scope of the present invention can be made using naturally occurring or non-naturally occurring amino acids. Whether or not natural or synthetic amino acids are used, it is preferred that only L-amino acids are present. Whatever amino acid changes are made (whether by means of substitution, insertion or deletion), preferred polypeptides of the present invention have at least 50% sequence identity with a polypeptide as defined in a) above, more preferably the degree of sequence identity is at least 75%. Sequence identities of at least 80%, at least 85%, at least 90%, at least 95% or at least 98% are most preferred.

The term "identity" can be used to describe the similarity between two polypeptide sequences. The degree of amino acid sequence identity can be calculated using a program such as "bestfit" (Smith and Waterman (1981) Advances in Applied Mathematics, 482-489) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M. O., Ed pp 353-358.

A software package well known in the art for carrying out this procedure is the CLUSTAL program. It compares the amino acid sequences of two polypeptides and finds the optimal alignment by inserting spaces in either sequence as appropriate. The amino acid identity or similarity (identity plus conservation of amino acid type) for an optimal alignment can also be calculated using a software package such as BLASTx. This program aligns the largest stretch of similar sequence and assigns a value to the fit. For any one pattern comparison, several regions of similarity may be found, each having a different score. One skilled in the art will appreciate that two polypeptides of different lengths may be compared over the entire length of the longer fragment. Alternatively small regions may be compared. Normally sequences of the same length are compared for a useful comparison to be made. Where high degrees of sequence identity are present there will be relatively few differences in amino acid sequence. Thus for example they may be less than 20, less than 10, or even less than 5 differences.

Polypeptides within the Scope of (c)

As discussed supra, it is often advantageous to reduce the length of a polypeptide, provided that the resultant reduced length polypeptide still has a desired activity or can give rise to useful antibodies. Feature (c) of the present invention therefore covers fragments of polypeptides (a) or (b) above. The skilled person can determine whether or not a particular fragment has activity using the techniques disclosed above.

Preferred fragments are at least 10 amino acids long. They may be at least 20, at least 50 or at least 100 amino acids long.

As will be discussed below, CD27L polypeptides will find use in an immunotherapeutic approach to epithelial-derived cancer. The skilled person will appreciate that for the preparation of one or more CD27L polypeptides, the preferred approach will be based on recombinant DNA techniques.

In order to more fully appreciate the present invention, nucleic acids within the scope of (d)-(h) above will now be discussed in greater detail.

CD27L polypeptides can be coded for by a large variety of nucleic acid molecules, taking into account the well known degeneracy of the genetic code. All of these molecules can be utilised in the present invention. They can be inserted into vectors and cloned to provide large amounts of DNA or RNA for further study. Suitable vectors may be introduced into host cells to enable the expression of polypeptides of the present invention using techniques known to the person skilled in the art.

Techniques for cloning, expressing and purifying polypeptides are well known to the skilled person. DNA constructs can readily be generated using methods well known in the art. These techniques are disclosed, for example in Sambrook et al, *Molecular Cloning 2$^{nd}$ Edition*, Cold Spring Harbour Laboratory Press (1989); in Old & Primrose *Principles of Gene Manipulation* 5th Edition, Blackwell Scientific Publications (1994); and in Stryer [*Biochemistry* 4th Edition, W H Freeman and Company (1995)]. Modifications of DNA constructs and the proteins expressed such as the addition of promoters, enhancers, signal sequences, leader sequences, translation start and stop signals and DNA stability controlling regions, or the addition of fusion partners may then be facilitated.

Normally the DNA construct will be inserted into a vector, which may be of phage or plasmid origin. Expression of the protein is achieved by the transformation or transfection of the vector into a host cell which may be of eukaryotic or prokaryotic origin. Such vectors and suitable host cells form third and fourth aspects of the present invention.

Knowledge of the nucleic acid structure can be used to raise antibodies and for gene therapy. Techniques for this are well-known by those skilled in the art.

By using appropriate expression systems, CD27L polypeptides may be expressed in glycosylated or non-glycosylated form. Non-glycosylated forms can be produced by expression in prokaryotic hosts, such as *E. coli*.

Polypeptides comprising N-terminal methionine may be produced using certain expression systems, while in others the mature polypeptide will lack this residue.

Preferred techniques for cloning, expressing and purifying a CD27L polypeptide are summarised below.

Polypeptides may be prepared natively or under denaturing conditions and then subsequently refolded. Baculoviral expression vectors include secretory plasmids (such as pACGP67 from Pharmingen), which may have an epitope tag sequence cloned in frame (e.g. myc, V5 or His) to aid detection and allow for subsequent purification of the protein. Mammalian expression vectors may include pCDNA3 and pSecTag (both Invitrogen), and pREP9 and pCEP4 (invitrogen). *E. coli* systems include the pBad series (His tagged—Invitrogen) or pGex series (Pharmacia).

The term "identity" can be used to describe the similarity between two individual DNA sequences. The 'bestfit' program (Smith and Waterman, Advances in Applied Mathematics, 482-489 (1981)) is one example of a type of computer software used to find the best segment of similarity between two nucleic acid sequences, whilst the GAP program enables sequences to be aligned along their whole length and finds the optimal alignment by inserting spaces in either sequence as appropriate. It is preferred if sequences which show substantial identity with any of those of (d), (e) or (f) have e.g. at least 50%, at least 75%, at least 80%, at least 85%, at least 90%, at least 95% or at least 98% sequence identity.

In addition to nucleic acid molecules coding for CD27L polypeptides, referred to herein as "coding" nucleic acid molecules, the present invention also includes nucleic acid molecules complementary thereto. Thus, for example, both strands of a double stranded nucleic acid molecule may be utilised in the present invention (whether or not they are associated with one another). Also included are mRNA molecules and complementary DNA Molecules (e.g. cDNA molecules).

Nucleic acid molecules which can hybridise to any of the nucleic acid molecules discussed above may also be utilised by the present invention. Such nucleic acid molecules are referred to herein as "hybridising" nucleic acid molecules. Hybridising nucleic acid molecules can be useful as probes or primers, for example. Desirably such hybridising molecules are at least 10 nucleotides in length and preferably are at least 25 or at least 50 nucleotides in length. The hybridising nucleic acid molecules preferably hybridise to nucleic acids within the scope of (d), (e), (f) or (g) above specifically. Desirably the hybridising molecules will hybridise to such molecules under stringent hybridisation conditions. One example of stringent hybridisation conditions is where attempted hybridisation is carried out at a temperature of from about 35° C. to about 65° C. using a salt solution which is about 0.9 molar. However, the skilled person will be able to vary such conditions as appropriate in order to take into account variables such as probe length, base composition, type of ions present, etc.

Manipulation of the DNA encoding the protein is a particularly powerful technique for both modifying proteins and for generating large quantities of protein for purification purposes. This may involve the use of PCR techniques to amplify a desired nucleic acid sequence. Thus the sequence data provided herein can be used to design primers for use in PCR so that a desired sequence can be targeted and then amplified to a high degree. Typically primers will be at least five nucleotides long and will generally be at least ten nucleotides long (e.g. fifteen to twenty-five nucleotides long). In some cases, primers of at least thirty or at least thirty-five nucleotides in length may be used.

As a further alternative, chemical synthesis may be used. This may be automated. Relatively short sequences may be chemically synthesised and ligated together to provide a longer sequence. In addition to being used as primers and/or probes, hybridising nucleic acid molecules of the present invention can be used as anti-sense molecules to alter the expression of CD27L polypeptides by binding to complementary nucleic acid molecules. This technique can be used in anti-sense therapy. A hybridising nucleic acid molecule of the present invention may have a high degree of sequence identity along its length with a nucleic acid molecule within the scope of (d)-(h) above (e.g. at least 50%, at least 75%, at least 80%, at least 85%, at least 90%, at least 95% or at least 98% sequence identity). As will be appreciated by the skilled person, the higher the sequence identity a given single stranded nucleic acid molecule has with another nucleic acid molecule, the greater the likelihood that it will hybridise to a nucleic acid molecule which is complementary to that other nucleic acid molecule under appropriate conditions.

The term 'RNA equivalent' when used above indicates that a given RNA molecule has a sequence which is complementary to that of a given DNA molecule, allowing for the fact that in RNA 'U' replaces 'T' in the genetic code. The nucleic acid molecule may be in isolated, recombinant or chemically synthetic form.

In view of the foregoing description the skilled person will appreciate that a large number of nucleic acids are within the scope of the present invention. Unless the context indicates otherwise, nucleic acid molecules of the present invention may additionally have one or more of the following characteristics:

they may be single or double stranded;
they may be provided in recombinant form i.e. covalently linked to a 5' and/or a 3' flanking sequence to provide a molecule which does not occur in nature;
they may be provided without 5' and/or 3' flanking sequences which normally occur in nature; and
they may be provided in substantially pure form. Thus they may be provided in a form which is substantially free from contaminating proteins and/or from other nucleic acids;

As described herein, CD27L is associated with epithelial-derived cancer, in particular kidney cancer and/or colorectal cancer, and as such provides a means of detection and/or diagnosis. In one embodiment, a convenient means for such detection, quantifying, screening, diagnosis, prophylaxis, or therapeutic treatment, will involve the use of antibodies. Thus, the CD27L polypeptides also find use in raising antibodies. Thus, in a further aspect, the present invention utilises antibodies, which bind to a CD27L polypeptide. Preferred antibodies bind specifically to CD27L polypeptides so that they can be used to purify and/or inhibit the activity of such polypeptides.

Thus, CD27L polypeptides may be used as immunogens to generate antibodies which immunospecifically bind a CD27L polypeptide. These are referred to herein as CD27L antibodies. CD27L antibodies include, but are not limited to polyclonal, monoclonal, bispecific, humanised or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein refers to immunoglobulin molecules and immunologically active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

In the production of antibodies, screening for the desired antibody can be accomplished by techniques known in the art, e.g. ELISA (enzyme-linked immunosorbent assay). For example, to select antibodies which recognise a specific domain of a CD27L polypeptide, one may assay generated hybridomas for a product which binds to a polypeptide fragment containing such domain. For selection of an antibody that specifically binds a first polypeptide homolog but which does not specifically bind to (or binds less avidly to) a second polypeptide homolog, one can select on the basis of positive binding to the first polypeptide homolog and a lack of binding to (or reduced binding to) the second polypeptide homolog.

For preparation of monoclonal CD27L antibodies (mAbs), any technique that provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, mAbs can be produced in germ-free animals utilising known technology (PCT/US90/02545).

The mAbs include but are not limited to human mAbs and chimeric mAbs (e.g., human-mouse chimeras). A chimeric antibody is a molecule in which different portions are derived from different animal species, such as those having a human immunoglobulin constant region and a variable region derived from a murine mAb. (See, U.S. Pat. No. 4,816,567; and U.S. Pat. No. 4,816,397, which are incorporated herein by reference in their entirety.) Humanised antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.)

Chimeric and humanised mAbs can be produced by recombinant DNA techniques known in the art, for example using methods described in WO 87/02671; EP 184,187; EP 171,496; EP 173,494; WO 86/01533; U.S. Pat. No. 4,816,567; EP 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559; Morrison (1985) Science 229:1202-1207; Oi et al. (1986,) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunised in the normal fashion with a selected antigen, e.g., all or a portion of a CD27L polypeptide. MAbs directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human mAbs and protocols for producing such antibodies, see, e.g., U.S. Pat. Nos. 5,625,126; 5,633,425; 5,569,825; 5,661,016; and 5,545,806. Completely human antibodies which recognise a selected epitope can be generated using a technique referred to as "guided selection." In this approach a selected non-human monoclonal antibody, e.g., a mouse antibody, is used to guide the selection of a completely human antibody recognising the same epitope. (Jespers et al. (1994) Bio/technology 12:899-903).

The CD27L antibodies can also be generated using various phage display methods known in the alt. In phage display methods, functional antibody domains are displayed on the surface of phage particles which carry the polynucleotide sequences encoding them. In a particular, such phage can be utilised to display antigen binding domains expressed from a repertoire or combinatorial antibody library (e.g., human or murine). Phage expressing an antigen binding domain that binds the antigen of interest can be selected or identified with antigen, e.g., using labelled antigen or antigen bound or captured to a solid surface or bead. Phage used in these methods are typically filamentous phage including fd and M13 binding domains expressed from phage with Fab, Fv or disulfide stabilised Fv antibody domains recombinantly fused to either the phage gene III or gene VIII protein. Phage display methods that can be used to make the antibodies of the present invention include those disclosed in Brinkman et al (1995) J. Immunol. Methods 182:41-50; Ames et al. (1995) J. Immunol. Methods 184:177-186; Kettleborough et al. (1994) Eur. J. Immunol. 24:952-958; Persic et al. (1997) Gene 187 9-18; Burton et al. (1994) Advances in Immunology 57:191-280; PCT Application No. PCT/GB91/01134; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in WO 92/22324; Mullinax et al. (1992) BioTechniques 12(6):864-869; and Sawai et al. (1995) AJRI 34:26-34 and Better et al. (1988) Science 240:1041-1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46-88 Shu et al. (1993) PNAS 90:7995-7999; and Skerra et al. (1988) Science 240:1038-1040.

The invention further provides for the use of bispecific antibodies, which can be made by methods known in the art. Traditional production of full length bispecific antibodies is based on the co-expression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details for generating bispecific antibodies see, for example, Suresh et al., Methods in Enzymology, 1986, 121:210.

The invention also utilises functionally active fragments, derivatives or analogs of the CD27L antibodies. Functionally active means that the fragment, derivative or analog is able to elicit anti-anti-idiotype antibodies (i.e., tertiary antibodies) that recognise the same antigen that is recognised by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognises the antigen. To determine which CDR sequences bind the antigen, synthetic peptides containing the CDR sequences can be used in binding assays with the antigen by any binding assay method known in the art.

The present invention utilises antibody fragments such as, but not limited to, F(ab')2 fragments and Fab fragments. Antibody fragments which recognise specific epitopes may be generated by known techniques. F(ab')2 fragments consist of the variable region, the light chain constant region and the CH1 domain of the heavy chain and are generated by pepsin digestion of the antibody molecule. Fab fragments are generated by reducing the disulfide bridges of the F(ab')2 fragments. The invention also provides heavy chain and light chain dimmers of the antibodies of the invention, or any minimal fragment thereof such as Fvs or single chain antibodies (SCAs) (e.g., as described in U.S. Pat. No. 4,946,778; Bird (1988) Science 242:423-42; Huston et al. (1988) Proc. Natl. Acad. Sci. USA 85:5879-5883; and Ward et al. (1989) Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in E. coli may be used (Skerra et al. (1988) Science 242:1038-1041).

In other embodiments, the invention utilises fusion proteins of the CD27L antibodies (or functionally active fragments thereof), for example in which the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. Preferably the CD27L antibody, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The antibodies for use in the invention include analogues and derivatives that are modified, for example but without limitation, by the covalent attachment of any type of molecule. Preferably, said attachment does not impair immunospecific binding. In one aspect, an antibody can be conjugated to a second antibody to form an antibody heteroconjugate (see U.S. Pat. No. 4,676,980). In other embodiments, the invention provides the therapeutic use of fusion proteins of the antibodies (or functionally active fragments thereof), for example but without limitation, where the antibody or fragment thereof is fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. In another aspect, an antibody fusion protein may facilitate depletion or purification of a polypeptide as described herein, increase half-life in vivo, and enhance the delivery of an antigen across an epithelial barrier to the immune system. Where the fusion protein is an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/06231, WO 92/22583, WO 90/09195, WO 89/01476, WO 99/15549 and WO03/031581. Alternatively, where the effector or reporter molecule is a protein or polypeptide the linkage may be achieved using recombinant DNA procedures, for example as described in WO 86/01533 and EP 0392745. Other effector groups include dextran, human serum albumin and hydroxypropylmethacrylamide (HPMA). Most preferably antibodies are attached to poly(ethyleneglycol) (PEG) moieties. Preferably, a modified Fab fragment is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one embodiment, a PEG modified Fab fragment has a maleimide group covalently linked to a single thiol group in a modified hinge region. A lysine residue may be covalently linked to the maleimide group. To each of the amine groups on the lysine residue may be attached a methoxypoly(ethyleneglycol) polymer having a molecular weight of approximately 20,000 Da. The total molecular weight of the entire effector molecule may therefore be approximately 40,000 Da.

The CD27L antibodies utilised include analogs and derivatives that are either modified, i.e., by the covalent attachment of any type of molecule as long as such covalent attachment that does not impair immunospecific binding. For example, but not by way of limitation, the derivatives and analogs of the CD27L antibodies include those that have been further modified, e.g., by glycosylation, acetylation, pegylation, phosphylation, amidation, derivatisation by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing CD27L antibodies can be used in methods known in the art relating to the localisation and activity of the CD27L polypeptides, e.g., for imaging or radioimaging these proteins, measuring levels thereof in appropriate physiological samples, in diagnostic methods, etc. and for radiotherapy.

The CD27L antibodies can be produced by any method known in the art for the synthesis of antibodies, in particular, by chemical synthesis or by recombinant expression, and are preferably produced by recombinant expression technique.

Recombinant expression of CD27L antibodies, requires construction of a nucleic acid that encodes the antibody. If the nucleotide sequence of the antibody is known, a nucleic acid encoding the antibody may be assembled from chemically synthesised oligonucleotides (e.g., as described in Kutmeier et al. (1994) BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridisable to the 3' and 5' ends of the sequence or by cloning using an oligonucleotide probe specific for the particular gene sequence.

If an antibody molecule that specifically recognises a particular antigen is not available (or a source for a cDNA library for cloning a nucleic acid encoding such an antibody), antibodies specific for a particular antigen may be generated by any method known in the art, for example, by immunising an animal, such as a rabbit, to generate polyclonal antibodies or, more preferably, by generating monoclonal antibodies. Alternatively, a clone encoding at least the Fab portion of the antibody may be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g., WO 86/05807; WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCR based methods, etc.

In addition, techniques developed for the production of "chimeric antibodies" (Morrison et al. (1984) Proc. Natl. Acad. Sci. 81:851-855; Neuberger et al. (1984) Nature 312: 604-608; Takeda et al. (1985) Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanised antibodies.

Once a nucleic acid encoding a CD27L antibody has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990), Molecular Cloning, A Laboratory Manual, 2d Ed., Cold Spring Harbor Laboratory, Cold Spring Harbor, N.Y.) and Ausubel et al. (eds., 1998, Current Protocols in Molecular Biology, John Wiley & Sons, N.Y.).

The expression vector is transferred to a host cell by conventional techniques and the transfected cells are then cultured by conventional techniques to produce an antibody of the invention.

The host cells used to express a recombinant CD27L antibody may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus is an effective expression system for antibodies (Foecking et al. (1998) Gene 45: 101; Cockett et al. (1990) Bio/Technology 8:2).

A variety of host-expression vector systems may be utilised to express a CD27L antibody. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, HEK 293, 3T3 cells) harbouring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the E. coli expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) may be utilised.

As discussed above, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein.

For long-term, high-yield production of recombinant CD27L antibodies, stable expression is preferred. For example, cells lines that stably express a CD27L antibody can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines may be particularly useful in screening and evaluation of agents that interact directly or indirectly with the antibody molecule.

The expression levels of the antibody molecule can be increased by vector amplification (for a review, see Bebbington and Hentschel. The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the CD27L antibody molecule has been recombinantly expressed, it may be purified by any method known in the alt for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilising an antibody specific for the fusion protein being expressed. For example, a system described by Janknecht et al. allows for the ready purification of non-denatured fusion proteins expressed in human cell lines (Janknecht et al. (1991 Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitrilo-acetic acid-agarose columns and histidine-tagged proteins are selectively eluted with imidazole-containing buffers.

In a preferred embodiment, CD27L antibodies or fragments thereof are conjugated to a diagnostic or therapeutic moiety. The CD27L antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$.

CD27L antibodies can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin, maytansinoids (e.g. DM1); an auristatin such as auristatin E or monomethylauristatin E or other auristatin derivative; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin, angiogenin, gelonin, dolstatins, minor groove-binders, bis-iodo-phenol mustard; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor. Other therapeutic moieties may include radionuclides such as $^{131}$I, $^{111}$In and $^{90}$Y, Lu$^{177}$, Bismuth212, Bismuth213, Californium$^{252}$, Iridium$^{192}$ and Tunsten$^{188}$/Rhenium$^{188}$, $^{211}$astatine; or drugs such as but not limited to, alkylphosphocholines, topoisomerase I inhibitors, taxoids and suramin. Therapeutic agents also include cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vinca alkaloids, e.g. vincristine, vinblastine, 4-desacetylvinblastine-3-carbohydrazide, vindesine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, but are not limited to, anti-folates (e.g. aminopterin and methotrexate), antimetabolites (e.g. methotrexate, 6-mercaptopurine, 6-thioguanine, cytarabine, 5-fluorouracil decarbazine, 5-fluoro-2'-deoxyuridine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin, adriamycin, idarubicin, morpholinodoxorubicin, epirubicin, doxorubicin hydrazides), antibiotics (e.g. dactinomycin (formerly actinomycin), bleomycin, mithramycin, anthramycin (AMC), calicheamicins or duocarmycins, CC-1065, enediyenes, neocarzinostatin), and anti-mitotic agents (e.g. vincristine and vinblastine). See Garnett, 2001, Advanced drug Delivery Reviews 53:171-216 for further details.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described in U.S. Pat. No. 4,676,980.

An antibody with or without a therapeutic moiety conjugated to it can be used as a therapeutic that is administered alone or in combination with cytotoxic factor(s) and/or cytokine(s).

The methods of diagnosis according to the present invention may be performed using a number of methods known to those skilled in the art, including, without limitation, immunoprecipitation followed by sodium dodecyl sulfate polyacrylamide gel electrophoresis, 2 dimensional gel electrophoresis, immunocytochemistry, immunohistochemistry, immunoassays, e.g. western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

The invention also provides diagnostic kits, comprising a capture reagent (e.g. an antibody) against a CD27L polypeptide as defined above. In addition, such a kit may optionally comprise one or more of the following:

(1) instructions for using the capture reagent for diagnosis, prognosis, therapeutic monitoring or any combination of these applications;
(2) a labelled binding partner to the capture reagent;
(3) a solid phase (such as a reagent strip) upon which the capture reagent is immobilised; and
(4) a label or insert indicating regulatory approval for diagnostic, prognostic or therapeutic use or any combination thereof.

If no labelled binding partner to the capture reagent is provided, the anti-polypeptide capture reagent itself can be labelled with a detectable marker, e.g. a chemiluminescent, enzymatic, fluorescent, or radioactive moiety (see above).

In a further embodiment, a diagnostic kit is provided comprising in one or more containers a pair of primers that under appropriate reaction conditions can prime amplification of at least a portion of a CD27L nucleic acid molecule, such as by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art. Typically, primers are at least five nucleotides long and will preferably be at least ten to twenty-five nucleotides long and more preferably fifteen to twenty-five nucleotides long. In some cases, primers of at least thirty or at least thirty-five nucleotides in length may be used.

The biological sample can be obtained from any source, such as a serum sample or a tissue sample, e.g. kidney or colon tissue. When looking for evidence of metastasis, one would look at major sites of kidney cancer or colorectal cancer metastasis, such as lymph nodes, liver, and pancreas.

In a further embodiment, the present invention provides methods for screening for anti-epithelial-derived cancer agents that modulate the expression or activity of a CD27L polypeptide or the expression of a CD27L nucleic acid. These agents may be useful in the treatment of epithelial-derived cancer. An exemplary agent of utility in the treatment of an epithelial-derived cancer, particularly wherein CD27L is over-expressed (e.g., expressed at levels higher than those observed in non-transformed cells of a similar tissue type), is an antibody capable of decreasing the activity and/or expression of CD27L. An exemplary antibody capable of down-regulating CD27L expression/activity is described in Example 6.

In a further aspect, the present invention provides methods for screening for anti-epithelial-derived cancer agents that interact with a CD27L polypeptide or a CD27L nucleic acid.

Agents can be selected from a wide variety of candidate agents. Examples of candidate agents include but are not limited to, nucleic acids (e.g. DNA and RNA), antibodies, carbohydrates, lipids, proteins, polypeptides, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683).

Examples of suitable methods based on the present description for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, for example, presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In one embodiment, agents that modulate the expression of a polypeptide are identified in a cell-based assay system. Accordingly, cells expressing a CD27L polypeptide are contacted with a candidate agent or a control agent and the ability of the candidate agent to alter expression of the CD27L polypeptide is determined. In a further embodiment, the expression of the CD27L polypeptide may be compared to a reference range or control. If desired, this assay may be used to screen a plurality (e.g. a library) of candidate agents. The cell, for example, can be of prokaryotic origin (e.g. *E. coli*) or eukaryotic origin (e.g. yeast or mammalian). Further, the cells can express a CD27L polypeptide endogenously or be genetically engineered to express a CD27L polypeptide. The ability of the candidate agents to alter the expression of a CD27L polypeptide can be determined by methods known to those of skill in the art, for example and without limitation, by flow cytometry, radiolabelling, a scintillation assay, immunoprecipitation or western blot analysis.

In another embodiment, a cell-based assay system is used to identify agents capable of modulating the activity of a CD27L polypeptide. In such an assay, the activity of a CD27L polypeptide is measured in a population of cells that naturally or recombinantly express a CD27L polypeptide, in the presence of a candidate agent. In such an assay, the activity of a CD27L polypeptide is measured in a population of cells that naturally or recombinantly express a CD27L polypeptide, in the presence of agent and in the absence of a candidate agent (e.g. in the presence of a control agent) and the activity of the CD27L polypeptide is compared. The candidate agent can then be identified as a stimulator or inhibitor of the activity of a CD27L polypeptide based on this comparison. In a further embodiment, the activity of a CD27L polypeptide can be measured in the presence or absence of a candidate agent. Preferably, the activity of a CD27L polypeptide is compared to a reference range or control.

In another embodiment, agents such as an enzyme, or a biologically active portion thereof, which is responsible for the production or degradation of a CD27L polypeptide, or is responsible for the post-translational modification of a CD27L polypeptide can be identified. In a primary screen, substantially pure, native or recombinantly expressed CD27L polypeptides or cellular extract or other sample comprising native or recombinantly expressed CD27L polypeptides are contacted with a plurality of candidate agents, for example but without limitation, a plurality of agents presented as a library, that may be responsible for the processing of a CD27L polypeptide, in order to identify such agents. The ability of the candidate agent to modulate the production, degradation or post-translational modification of a CD27L polypeptide can be determined by methods known to those of skill in the art, including without limitation, flow cytometry, radiolabelling, a kinase assay, a phosphatase assay, immunoprecipitation and western blot analysis.

In yet another embodiment, cells expressing a CD27L polypeptide are contacted with a plurality of candidate agents. The ability of such an agent to modulate the production, degradation or post-translational modification of a CD27L polypeptide can be determined by methods known to those of skill in the art, including without limitation, flow cytometry, radiolabelling, kinase assay, phosphatase assay, immunoprecipitation and Western blot analysis.

In one embodiment, agents that modulate the expression of a polypeptide are identified by contacting cells (e.g. cells of prokaryotic origin or eukaryotic origin) expressing a CD27L polypeptide with a candidate agent or a control agent (e.g. phosphate buffered saline; PBS) and determining the expression of a CD27L polypeptide or mRNA encoding a CD27L polypeptide. The level of expression of a CD27L polypeptide or mRNA encoding said polypeptide in the presence of the candidate agent is compared to the level of expression of a CD27L polypeptide or mRNA encoding said polypeptide in the absence of the candidate agent (e.g. in the presence of a control agent). The candidate agent can then be identified as a modulator of the expression of a CD27L polypeptide based on this comparison. For example, when expression of a CD27L polypeptide (or its mRNA) is significantly greater in the presence of the candidate agent than in its absence, the candidate agent is identified as a stimulator of expression of a CD27L polypeptide. Alternatively, when expression of a CD27L polypeptide (or its mRNA) is significantly less in the presence of the candidate agent than in its absence, the candidate agent is identified as an inhibitor of the expression of the polypeptide. The level of expression of a CD27L or its encoding mRNA can be determined by methods known to those of skill in the art. For example, mRNA expression can be assessed by Northern blot analysis or RT-PCR, and protein levels can be assessed, without limitation, by western blot analysis.

In another embodiment, agents that modulate the expression of a CD27L polypeptide are identified in an animal model. Examples of suitable animals include, but are not limited to, mice, rats, rabbits, monkeys, guinea pigs, dogs and cats. Preferably, the animal used represents a model of epithelial-derived cancer. In accordance with this embodiment, the candidate agent or a control agent is administered (e.g. orally, rectally or parenterally such as intraperitoneally or intravenously) to a suitable animal and the effect on the expression of a CD27L polypeptide (or its mRNA) is determined. Changes in the expression of a polypeptide can be assessed by the methods outlined above.

In yet another embodiment, a CD27L polypeptide is used as a "bait protein" in a two-hybrid assay or three hybrid assay to identify other proteins that bind to or interact with the polypeptide (see e.g. U.S. Pat. No. 5,283,317; Zervos et al., 1993, Cell 72:223-232; Madura et al. 1993, J. Biol. Chem. 268:12046-12054; Bartel et al., 1993, Bio/Techniques 14:920-924; Iwabuchi et al., 1993, Oncogene 8:1693-1696;

and WO 94/10300). As those skilled in the art will appreciate, such binding proteins are also likely to be involved in the propagation of signals by a CD27L polypeptide, for example, they may be upstream or downstream elements of a signalling pathway involving a CD27L polypeptide.

Alternatively, polypeptides that interact with a CD27L polypeptide can be identified by isolating a protein complex comprising a CD27L polypeptide and identifying the associated polypeptides using methods known in the art such as mass spectrometry (for examples see Blackstock, W. & Weir, M. 1999, Trends in Biotechnology, 17: 121-127; Rigaut, G. 1999, Nature Biotechnology, 17: 1030-1032; Husi, H. 2000, Nature Neurosci. 3:661-669; Ho, Y. et al., 2002, Nature, 415: 180-183; Gavin, A. et al., 2002, Nature, 415: 141-147).

One skilled in the art will also appreciate that a polypeptide may also be used in a method for the structure-based design of an agent, in particular a small molecule which acts to modulate (e.g. stimulate or inhibit) the activity of said polypeptide, said method comprising:

1) determining the three-dimensional structure of said polypeptide;
2) deducing the three-dimensional structure of the likely reactive or binding site(s) of the agent;
3) synthesising candidate agents that are predicted to react or bind to the deduced reactive or binding site; and
4) testing whether the candidate agent is able to modulate the activity of said polypeptide.

It will be appreciated that the method described above is likely to be an iterative process.

This invention further provides novel agents identified by the above-described screening methods and uses thereof for treatments as described herein.

As discussed herein, agents of the invention find use in the treatment of epithelial-derived cancer.

Thus, in an additional embodiment, the present invention provides a pharmaceutical composition comprising at least one agent of the invention, optionally together with one or more pharmaceutically acceptable excipients, carriers or diluents. In one aspect, the pharmaceutical composition is for use as a vaccine and so any additional components will be acceptable for vaccine use. In addition, the skilled person will appreciate that one or more suitable adjuvants may be added to such vaccine preparations.

As discussed herein, the CD27L polypeptides, CD27L nucleic acids and CD27L antibodies find use in the treatment or prophylaxis of epithelial-derived cancer. Thus, in another aspect, the present invention provides a pharmaceutical composition comprising at least one CD27L polypeptide, at least one CD27L nucleic acid or at least one CD27L antibody, optionally together with one or more pharmaceutically acceptable excipients, carriers or diluents for use in the diagnosis, treatment and/or prophylaxis of epithelial-derived cancer. In one embodiment the CD27L polypeptide is a dominant negative mutant. In a further embodiment, the CD27L polypeptide is constitutively active. Preferably, a pharmaceutical composition is for use as a vaccine and so any additional components will be acceptable for vaccine use. In addition, the skilled person will appreciate that one or more suitable adjuvants may be added to such vaccine preparations.

In one aspect, the present invention provides a method for the prophylaxis and/or treatment epithelial-derived cancer in a subject, which comprises administering to said subject a therapeutically effective amount of at least one CD27L polypeptide, CD27L nucleic acid or CD27L antibody. In another aspect, the present invention provides the use of at least one CD27L polypeptide, CD27L nucleic acid molecule or CD27L antibody in the preparation of a composition for use in the diagnosis, prophylaxis and/or treatment of epithelial-derived cancer.

The composition will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatin capsules include for example vegetable oils, waxes, fats, semi-solid, or liquid polyols etc. For the preparation of solutions and syrups, excipients which may be used include for example water, polyols and sugars. For the preparation of suspensions, oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research (1986) 3(6):318.

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulisers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilised) condition requiring only the addition of the sterile liquid carried, for example water for injections, immediately prior to use. Extemporaneous injection solutions and suspensions may be prepared from sterile powders, granules and tablets.

Sterile injectable solutions can be prepared by incorporating the agent in the required amount in an appropriate solvent with one or a combination of ingredients enumerated above, as required, followed by sterilization microfiltration.

In certain embodiments, the agents of the invention can be formulated to ensure proper distribution in vivo, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29: 685).

Exemplary targeting moieties include folate or biotin (see, e.g., U.S. Pat. No. 5,416,016); mannosides (Umezawa et al., (1988) Biochem. Biophys. Res. Commun. 153: 1038); antibodies (P. G. Bloeman et al. (1995) FEBSLett. 357: 140; M. Owais et al. (1995) Antimicrob. Agents Chemother. 39: 180); surfactant protein A receptor (Briscoe et al. (1995) Am. J. Physiol. 1233: 134), different species of which may comprise the formulations of the inventions, as well as components of the invented molecules; psi 20 (Schreier et al. (1994) J. Biol. Chem. 269: 9090); see also K. Keinanen; M. L. Laukkanen (1994) FEBSLett. 346: 123; J. J. Killion; I. J. Fidler (1994) Immunomethods 4: 273. In one embodiment of the invention, the agents of the invention are formulated in liposomes; in a more preferred embodiment, the liposomes include a targeting moiety. In a most preferred embodiment, the agents in the liposomes are delivered by bolus injection to a site proximal to the tumor.

The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The pharmaceutical compositions may contain preserving agents, solubilising agents, stabilising agents, wetting agents, emulsifiers, sweeteners, colourants, odourants, salts (agents of the present invention may themselves be provided in the form of a pharmaceutically acceptable salt), buffers, coating agents or antioxidants. They may also contain therapeutically active agents in addition to the agent of the present invention.

Dosages of the agent of the present invention can vary between wide limits, depending upon the disease or disorder to be treated, the age and condition of the individual to be treated, the age, weight and gender of the subject, diet, time and frequency of administration, drug combination(s), reaction sensitivities and tolerance/response to therapy and a physician will ultimately determine appropriate dosages to be used. This dosage may be repeated as often as appropriate. If side effects develop the amount and/or frequency of the dosage can be reduced, in accordance with normal clinical practice. The dosage can be determined by routine experimentation and is within the judgment of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose. Compositions may be administered individually to a patient or may be administered in combination (e.g. simultaneously, sequentially or separately) with other agents, drugs or hormones. The dose at which the antibody molecule of the present invention is administered depends on the nature of the condition to be treated, the extent of the inflammation present and on whether the antibody molecule is being used prophylactically or to treat an existing condition. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The following examples are presented in order to more fully illustrate the preferred embodiments of the invention. They should in no way be construed, however, as limiting the scope of the invention.

EXAMPLES

Example 1

Identification and Cloning of CD27L

Protein CD27L was isolated from A498 cell membranes. A498 is a renal epithelial carcinoma cell (ATCC no CRL-7908). This cell was grown in DMEM medium containing 10% fetal bovine serum and 2 mM L-glutamine. CD27L was also isolated from SW 839 renal cell carcinoma-derived cells (ATCC No. HTB-49). These cells were cultured in L15+10% FBS.

Cell Fractionation and Plasma Membrane Generation:

$10 \times 15$ cm$^2$ dishes of cells were washed three times with PBS-CM (each dish contained approx. $2 \times 10e8$ cells). 5 mls of ice cold PBS-CM was added to the first dish and the cells were scraped using a plastic cell lifter. All the dishes were scraped in this volume of PBS-CM. The cells were then centrifuged at 1000×g for 5 minutes at +4° C. The supernatant was removed and the cells were resuspended in 10 mls of homogenizing buffer (250 mM sucrose in 10 mM HEPES, 1 mM EDTA 1 mM Vanadate, 0.02% Azide). The cells were centrifuged at 1000×g for 5 minutes at +4° C. and the supernatant removed. The cell pellet was then resuspended in 5× packed cell volume with homogenizing buffer plus protease inhibitors (Sigma). The ball bearing homogeniser (BBH) (8.002 mm ball) was chilled and rinsed with homogenizing buffer. The cell suspension was taken up in a 2 ml syringe and this was attached to one side of the BBH. Another syringe was attached to the other side of the BBH. The cell mixture was fed through the chamber up to five times. The cells were monitored using a microscope and when the cells were sufficiently lysed the resulting mixture was centrifuged at 1000×g for 5 minutes at +4°. The resulting supernatant (PNS) was retained. 1 ml of homogenizing buffer was added to the nuclear pellet and re-centrifuged at 1000×g for 5 minutes. The above two fractions were pooled and centrifuge at 3000×g for 10 minutes at +4° C. The 3000×g supernatant was layered onto 2 ml 60% sucrose cushion in SW40 or SW60 tube and centrifuged at 100,000×g for 45 minutes with slow acceleration and deceleration. The crude plasma membrane was evident as a discrete layer on top of the sucrose cushion. The upper layer was removed (cytosol) and the plasma membrane was collected using a pasteur pipette. The % sucrose of crude plasma membrane fraction was determined using a refractometer. The membrane preparation was diluted with HEPES buffer to reduce the sucrose content to below 15%. The crude plasma membrane preparation was layered on preformed 15 to 60% sucrose gradient in SW40 tube and spun at 100 000×g for 17 hours with slow acceleration and deceleration. The sucrose gradient was fractionated using the gradient unloader (speed 0.5, distance 2.5, fractions 35). The protein content of the fractions was measured and 10 micrograms of protein was run on a 4-20% acrylamide 1D gel (Novex) and subject to western blotting with antibodies to Transferrin Receptor, Oxidoreductase II and Calnexin.

Preparation of Plasma Membrane Fractions for 1D Gel Analysis:

The plasma membrane fractions were identified which had transferrin immunoreactivity but no oxidoreductase II or calnexin immunoreactivity. The sucrose fractions were pooled and diluted at least four times with 10 mM HEPES, 1 mM EDTA 1 mM vanadate, 0.02% azide. The diluted sucrose fraction was added to a SW40 or SW60 tube and centrifuged at 100,000×g for 45 minutes with slow acceleration and deceleration. The supernatant was removed from the membrane pellet and the pellet was washed three times with PBS-CM. The membrane pellet was solubilized in 2% SDS in 63 mM TrisHCL pH 7.4. A protein assay was done and mercaptoethanol (2% final), glycerol (10%) and bromopheneol blue (0.0025% final) was added. A final protein concentration of 1 microgram/microliter was used for 1D gel loading. The extracted protein sample was solubilized in 1D lysis buffer and the proteins separated by 1D PAGE (8-16% gradient).

Mass Spectrometry

CD27L protein excised from the 1D gel was digested with trypsin and analyzed by MALDI-TOF-MS (Voyager STR, Applied Biosystems) using a 337 nm wavelength laser for desorption and the reflection mode of analysis. Selected masses for CD27L ([M+H]=1217.6 and 1695.8) were further characterised by tandem mass spectrometry using a QTOF-MS equipped with a nano liquid chromatography system eluting directly into the instrument. Prior to MALDI analysis the samples were desalted and concentrated using C18 Zip TiPS™ (Millipore).

For partial amino acid sequencing and identification of CD27L, uninterpreted tandem mass spectra of tryptic peptides were searched using the SEQUEST search program (Eng et al., 1994, J. Am. Soc. Mass Spectrom. 5:976-989), version v.C.1. The database searched was a database constructed of protein entries in the non-redundant database held by the National Centre for Biotechnology Information (NCBI) which is accessible at http://www.ncbi.nlm.nih.gov/. The tandem amino acid sequences were found to match the protein CD27L (available under the accession number P32970 in the SwissProt database, held by the Swiss Institute of Bioinformatics, (http://www.expasy.ch/)) (FIG. 1). The predicted mass of the protein is 21.1 kDa, and the apparent molecular weight as measured on the gel is 23.7 kDa.

Example 2

Expression of CD27L mRNA in Human Tissues

Figure 3:
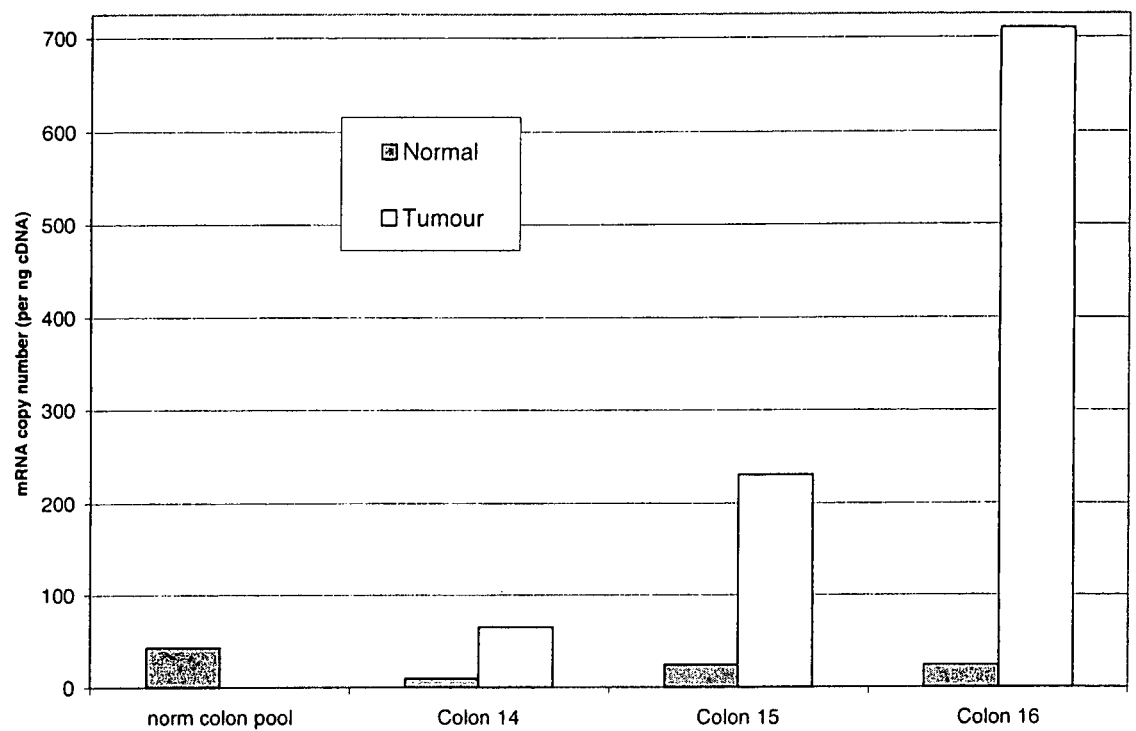
FIG. 3: shows the expression of CD27L in normal and tumour colon tissues. Levels of CD27L mRNA in matched normal and tumour tissues from three patients were measured by real time RT-PCR. mRNA levels are expressed as the number of copies $ng^{-1}$ cDNA.
Figure 4:
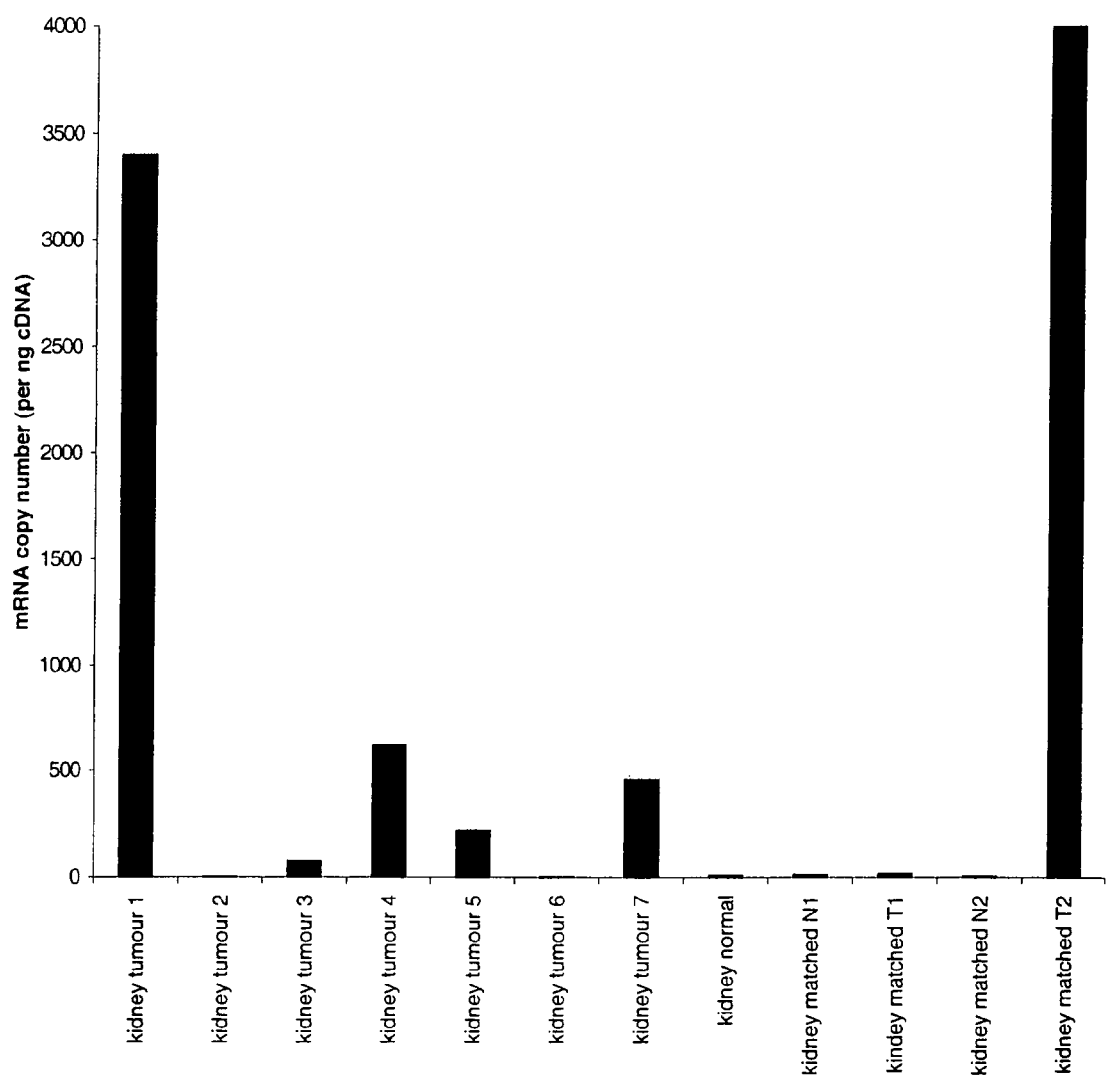
FIG. 4: shows the expression of CD27L in a number of kidney tumour tissues, including two pairs of matched normal and tumour tissues. Levels of CD27L mRNA were measured
Figure 5:
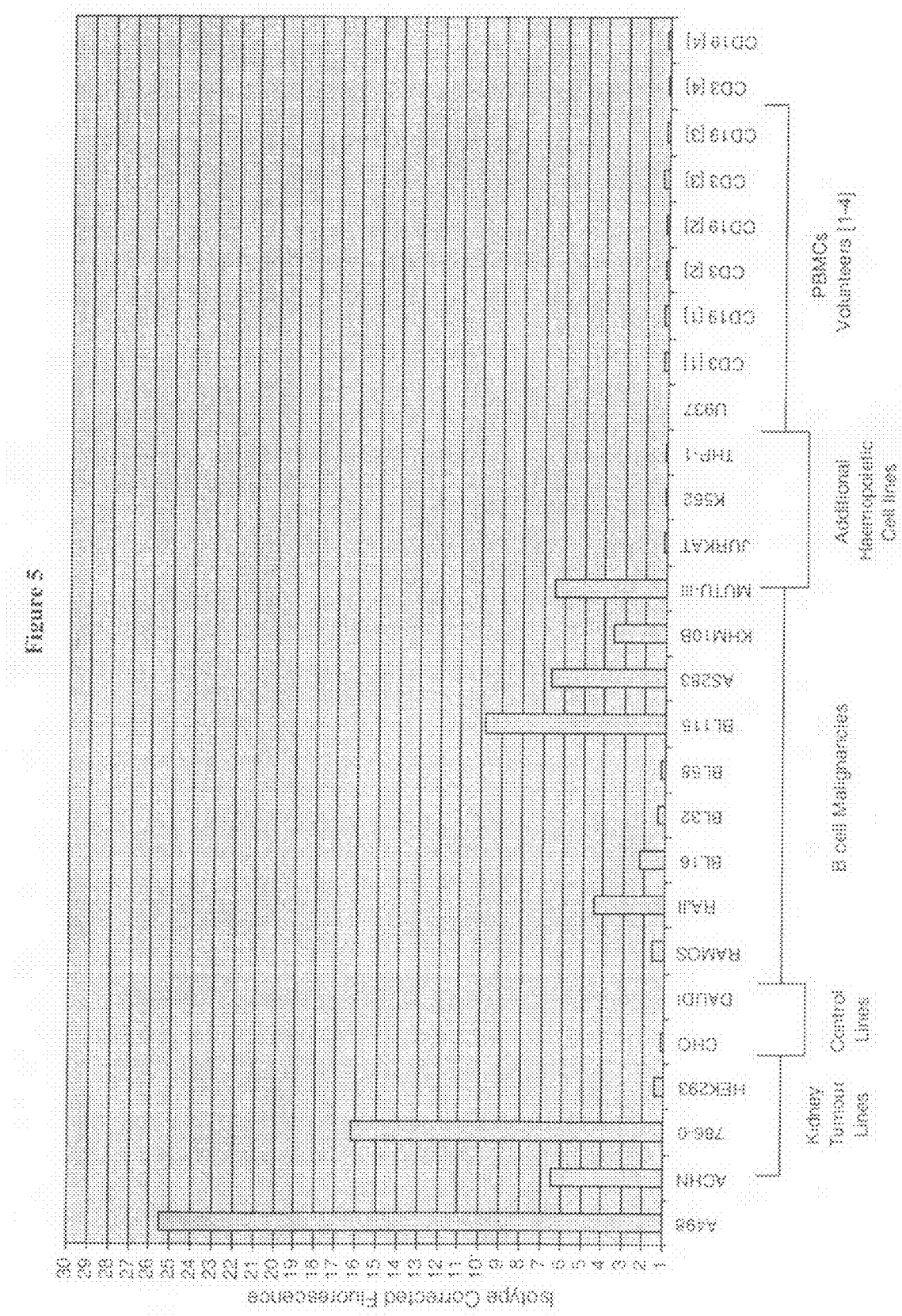
FIG. 5: shows the relative expression of CD27L estimated by flow cytometry using an FITC labelled anti-CD27L antibody.

We used real time quantitative RT-PCR (Heid et al. (1996) Genome Res. 6, 986-994; Morrison et al. (1998) Biotechniques 24: 954-958) to analyse the distribution of CD27L mRNA in normal human tissues, kidney cancer cell lines and kidney and colon cancer clinical tissues (FIGS. 2-4).

Preparation of Total RNA and First Strand cDNA Synthesis.

Total RNA was prepared from cultured cells and homogenised tissue samples using Trizol reagent (Life Technologies), according to the manufacturer's instructions, and resuspended in RNAse-free water at a concentration of 1 µg/µl. First strand cDNA was synthesised from 5 µg of total RNA using Superscript II reverse transcriptase (Life Technologies), according to the manufacturer's instructions. Each cDNA sample was purified using a PCR purification minicolumn (Qiagen), quantified by spectrophotometry at 260 nm, and diluted to 10 ng/µl.

Quantification of CD27L mRNA by RT-PCR

Real time RT-PCR was used to quantitatively measure CD27L expression in normal human tissue mRNAs (Clontech), kidney cancer cell lines, and kidney and colon cancer tissues. The primers used for PCR were as follows:

sense, 5' gctgctttggtcccattgctcg 3' (SEQ ID NO:3)
antisense, 5' gaggtcctgtgtgattcagctg 3' (SEQ ID NO:4)

Reactions containing 10 ng cDNA, prepared as described above, SYBR green sequence detection reagents (PE Biosystems) and sense and antisense primers were assayed on an ABI7700 sequence detection system (PE Biosystems). The PCR conditions were 1 cycle at 50° C. for 2 min, 1 cycle at 95° C. for 10 min, and 40 cycles of 95° C. for 15s, 65° C. for 1 min. The accumulation of PCR product was measured in real time as the increase in SYBR green fluorescence, and the data were analysed using the Sequence Detector program v1.6.3 (PE Biosystems). Standard curves relating initial template copy number to fluorescence and amplification cycle were generated using the amplified PCR product as a template, and were used to calculate CD27L copy number in each sample.

As shown in FIG. 2, the distribution of CD27L mRNA was low in normal tissues, with the highest levels of expression in thymus, tonsil and lymph node (147-200 copies $ng^{-1}$ cDNA), and only low levels of CD27L message detected in other normal tissues. CD27L mRNA was detected in the HEK 293 kidney cancer cell line (190 copies $ng^{-1}$ cDNA) and was highly overexpressed in Wilm's tumour cell line (kidney cancer in children, see supra) (9200 copies $ng^{-1}$ cDNA).

FIG. 3 shows the levels of expression of CD27L in 3 matched normal/tumour colon pairs, along with the expression in normal colon. The levels of expression are increased in all sample pairs, between 7 and 30 times.

FIG. 4 shows the level of expression of CD27L in seven kidney tumours, as well as in normal kidney tissues and in two matched pairs of tumour and normal kidney tissues. Elevated expression is observed in the majority of tumour samples, with levels in two samples above 3000 copies $ng^{-1}$ cDNA.

Example 3

The Relative Expression of CD27L was Estimated by Flow Cytometry Using an FITC Labelled Anti-CD27L Antibody Directly conjugated anti-CD27L antibody was obtained from Ancell Corp (Bayport, USA). This IgG1 antibody (designated BU69) was derived via immunisation of mice with the WM-1 (Waldenström's macroglobulinemia) cell line. The binding epitope has not been identified, however this antibody has been shown to inhibit T cell proliferation induced by dendritic cells and can therefore be viewed as 'neutralising', (see Leukocyte Typing V, S. F. Schlossman, et al, eds. Oxford University Press, Oxford, (1995) p. 1137-1138). The isotype control used was an FITC labelled IgGk1 antibody obtained from Serotec Ltd (Kidlington, UK). The following B cell lines: BL16, BL32, BL58, BL115, AS283 and KHM10B were provided by Prof. Martin Dyer (University of Leicester) whereas the MUTU-III line was provided by Dr. Noemi Nagy (Karolinska Institute, Sweden). All other lines were purchased from the ECACC or ATCC.

Adherent cell lines were harvested using standard non-enzymatic dissociation solution (Sigma). Suspension cells were harvested by removal of an appropriate amount of culture media from the flask. For peripheral blood mononuclear cell (PBMC) preparation; buffy coat preparations were obtained from the national blood service (NBS —John Radcliffe branch, Oxford, UK) under the terms of agreement 0211/T464. Pure cell suspensions were subsequently purified by centrifugation over Ficoll gradients (Sigma) according to the manufacturers instructions. Platelets were then depleted from PBMC cell suspensions by 4 rounds of low-speed centrifugation. All cell lines (adherent, suspension and primary volunteer PBMCs) were then washed a further time in DPBS, counted using a haemocytometer and resuspended at 5 million cells $ml^{-1}$.

Flow Cytometry Protocol

For all cells to be analysed, a 100 µl aliquot of cells ($5 \times 10^5$ cells) was added to each well on a 96 well plate. The cells were then pelleted by centrifugation at 2 krpm for 5 minutes and each pellet resuspended in 40 µl of DPBS supplemented with 0.5% BSA. The plate was then incubated at 4 degrees for 20 minutes to allow blocking of hydrophobic binding sites on the cell surface. After incubation, 10 µl of anti-CD27L antibody was added which had been previously diluted 1/10 from the original stock using DPBS [originally 1 µl per test, here using 10 µl per test]. For all cells an additional sample was prepared in parallel, where the anti-CD27L antibody was substituted for a 10 µl aliquot of IgG1k FITC isotype control antibody (Serotec Ltd.). The antibody labelled cells were then incubated for 1 hour at room temperature, with intermittent mixing (every 15 minutes). After incubation, cell were washed 3 times in standard DPBS and placed into polystyrene FACS tubes [Elkay Ltd.]. All flow cytometry acquisition was performed using an EPICS XL flow cytometer [Coulter Corp]. Cellular fluorescence was detected in FL1, cell aggregates were removed from the analysis by FSC/SSC gating. For data analysis, the [log] mean fluorescence intensity of the isotype control sample was subtracted from the [log] mean fluorescence intensities for the same cell line. This value, termed 'isotype corrected fluorescence' was then plotted for each cell line or peripheral blood sample and displayed in the form of a bar-chart. Standard errors not exceeding +/−10% were viewed as acceptable for these experiments.

Results

All kidney cell lines tested were found to express a significant level of CD27L. For two cell lines (A498 and 786-0) this fluorescence was the highest seen in the entire panel of cell lines. Amongst the B cell lines tested there was considerable variability in the levels of CD27L detected, with some cells not expressing at all. The human embryonic kidney line HEK-293 was also shown to be negative, as was the CHO cell line, included as an negative control. A T cell derived cell line (Jurkat), a myeloid leukemia line (K562) and two monocytic cell lines (U937 and THP-1) were also found to be negative for CD27L. With respect to peripheral blood subsets, for all 4 volunteers, both the CD3+ [T cell] and CD19+(B cell) subsets were found to be CD27L negative.

Therefore, kidney cell lines have considerably higher CD27L expression than peripheral blood T and B cells. CD27L expression can be detected on a high proportion of B cell malignancies but not on myeloid lines. These findings suggest that a potential therapeutic antibody delivered into the circulation will not be sequestered by B/T cells expressing CD27L. Therefore, CD27L expression is most probably restricted to activated cells within lymphoid tissue i.e. Lymph node, Spleen, Tonsils etc.

Example 4

Summary: Binding of an Anti-CD27L Antibody to a Panel of Kidney Tumour Cell Lines Directly conjugated anti-CD27L antibody was obtained from Ancell Corp (Bayport, USA) as described above.

Cell lines were harvested by trypsin digestion and re-seeded onto chamber slides. After 24 hours incubation the chambers were washed three time in PBS and resuspended in 5% Formaldehyde to fix. After 5 minutes fixation, cells were washed a further three times in DPBS and blocked in DPBS supplemented with 5% FBS. The cells were pre-blocked for 60 minutes to prevent non-specific binding of antibody to cells. Primary FITC conjugated antibody (either anti-CD27L or IgG1 isotype control) was then added (1 µg/ml in a 200 µl 5% FBS DPBS) and the chamber slides incubated overnight at 4° C. Following incubation the cells were washed twice in DPBS/5% and once with DPBS alone, leaving at least 5 minutes between each wash step. The slides were then mounted in aqueous mounting media and visualised using a DMRIE2 fluorescence microscope (Leica AG).

For all four kidney tumour lines tested there was some element of reactivity with the anti-CD27L FITC antibody. The strongest CD27L staining was observed on A489 cells. Both control lines (CHO and HEK-293 cells) failed to show any specific fluorescence when incubated with anti-CD27L. A negligible signal was observed after incubation of all cell lines with the IgG1k-FITC control antibody.

Therefore, CD27L expression can be detected on all of the kidney tumour lines tested but was not found on the embryonic kidney line HEK-293 nor on the control CHO line.

Example 5

Immunohistochemical Analysis of CD27L Protein Expression in Clinical Normal and Cancer Tissues A range of normal frozen tissues (brain, breast, kidney, liver, tonsil, lymph nodes, skin, and thyroid) and tumour tissues were obtained from the Cellular Pathology Department at the John Radcliffe Hospital, Oxford, UK together with pre-sectioned primary and metastatic renal cell carcinoma tissue from Ardais Corporation, Lexington Mass., USA. Frozen sections of 8 µm were cut for each tissue on a cryostat (Leica Microsystems (UK) Ltd., Milton Keynes, Bucks, UK) and mounted on Snowcoat X-tra glass slides (Surgipath Europe Ltd., Peterborough, UK). Following air-drying for 30 minutes at room temperature each section was immersed in 100% acetone for 15 minutes, air dried and then stored at −20° C. until required.

Tissue sections were allowed to warm to room temperature and then immersed for 10 minutes in 3% hydrogen peroxide in water to quench endogenous peroxidase activity, followed by washing in water and then Tris-buffered saline (TBS) pH7.6. A monoclonal mouse anti-human CD27L antibody (DakoCytomation, Ely, UK) was applied to the tissues (2 µg/ml in TBS) for 90 minutes followed by two 5 minutes washes in TBS. Secondary antibody from the DakoCytomation Envision anti-mouse system (DakoCytomation, Ely, UK) was applied for 30 minutes followed by two washes in TBS. Detection was achieved by a 5 minute incubation in the presence of 3,3'-diaminobenzidine (DAB+) substrate chromogen which results in a brown coloured precipitate at the antigen site. Sections were counter stained in Gills II haematoxylin (Surgipath Ltd) and mounted under glass cover slips using aqueous mounting medium (Faramount, DakoCytomation, Ely, UK).

Immunohistochemistry on frozen tissue sections was used to determine expression of CD27L on a number of different types of normal and malignant tissues including 30 kidney cancer donor tissues. No CD27L expression was detected on the cell surface of any of the normal tissues tested. The results of the analysis of the tumour tissues are shown in Table 1. In total, 89 donor tumour tissues were examined and only the renal cell carcinoma tissues exhibited strong staining with the anti-CD27L antibody. As evidenced by detection of CD27L immunoreactivity in 16 of the 20 cases (80%) tested, this finding was particularly pronounced for the clear cell sub-type which comprises the majority (75%) of all renal cell carcinomas. Thus, CD27L is a good marker for the diagnosis of renal cell carcinoma, especially for the clear cell sub-type. Of all the other tumour tissues examined, only weak staining was observed in two out of four cases of lymphoblastic lymphoma, four out of six cases of large cell lymphoma, and one out of nine cases of lung adenocarcinoma (Table 1). Notably, examples of strong uniform CD27L immunostaining of the renal cell carcinoma tissues, but not other kidney cancer types or normal kidney, was observed.

Of those tumour tissues analysed as indicated in Table 1, several are not epithelial-derived, including: the brain, kidney (sarcomatoid and neuroblastoma), all categories of lymphoma, and the skin melanoma samples examined. In view of the relatively small sample number of some of the tumour types evaluated for CD27L expression, a more detailed analysis may be required to determine that the indicated tumour type is a bona fide CD27L non-expressor (i.e., does not express CD27L or expresses negligible amounts of CD27L). Additional analyses are also necessitated in order to exclude the possibility that certain sub-types of various tumour tissue types may be positive for CD27L expression. The identification of other tumour types or sub-types thereof that express CD27L may present additional opportunities for diagnostic and/or therapeutic intervention using methods similar to those described herein above for renal cell carcinoma.

The results to date demonstrate that CD27L displays a highly restricted expression pattern that underscores its utility as a positive diagnostic indicator for renal cell carcinoma. Moreover, it is a particularly useful diagnostic marker for the clear cell sub-type of renal cell carcinoma. The restricted expression pattern of CD27L also accentuates advantages in using this cell surface antigen as a target for therapeutic modalities, wherein, for example, an anti-CD27L antibody may be administered to a subject with renal cell carcinoma for the purposes of down-regulating expression and/or activity of CD27L. See Example 6 for additional details. In an alternative targeted therapeutic regimen, an anti-CD27L is coupled or conjugated directly to a drug moiety, such as, for example, a toxin (e.g., an auristatin, or other toxin mentioned supra), which upon internalisation of the antibody-toxin complex following binding to CD27L results in targeted cell death of CD27L positive cells. Alternatively, an anti-CD27L may be indirectly coupled or conjugated to a drug moiety, such as a cell toxin, via coupling to a second compound capable of interacting with the anti-CD27L antibody, wherein the second compound is linked directly to the toxin. See Example 6 for additional details and evidence further supportive of such regimens. The restricted expression pattern observed for CD27L indicates that side effects resulting from such therapeutic regimens will be minimal since cells that do not express CD27L should not be adversely affected by therapeutics that specifically target CD27L expressing cells.

Expression of CD27L was also examined in eleven renal cell carcinoma (clear cell sub-type) metastatic donor tissues, two of which had matched primary renal cell carcinoma (clear cell sub-type) tumour tissue for comparison. Eight of the eleven (73%) metastatic tissues showed some CD27L expression. Of note, the intensity of CD27L immunostaining was the same for the primary renal cell carcinoma (clear cell sub-type) and metastasis therefrom, isolated from the two donors with matched primary and metastatic tissues. These results indicate that metastases of CD27L positive primary tumour tissue may also be diagnosed using reagents for detecting CD27L expression and targeted using CD27L specific therapeutic modalities such as those described herein above for renal cell carcinoma.

TABLE 1

|  | Tumour type | No. of Cases | Positivity |
|---|---|---|---|
| Bladder - | Transitional cell carcinoma | 2 | — |
| Brain |  | 1 | — |
| Breast - | Primary invasive ductal carcinoma | 11 | — |
| Breast node - | Invasive carcinoma | 2 | — |
| Colon - | adenocarcinoma | 2 | — |
| Kidney - | Renal cell carcinoma, papillary | 3 | — |
|  | Renal cell carcinoma, clear cell | 20 | 16 |
|  | Oncocytoma (benign) | 1 | — |
|  | Sarcomatoid | 1 | — |
|  | Transitional cell carcinoma | 1 | — |
|  | Neuroblastoma | 1 | — |
|  | Wilms tumour | 30 | — |
| Liver - | Hepatoblastoma | 1 | — |
| Lymphoma - | Follicular | 8 | — |
|  | Lymphoblastic | 4 | 2 |
|  | Large cell lymphoma | 6 | 4 |
|  | B-chronic lymphoid leukemia | 2 | — |

TABLE 1-continued

| Tumour type | | No. of Cases | Positivity |
|---|---|---|---|
| Skin - | Melanoma | 1 | — |
| Thyroid - | adenocarcinoma | 1 | — |
| Lung - | Adenocarcinoma | 9 | 1 |
| | Squamous carcinoma | 8 | — |
| | Clear cell carcinoma | 1 | — |

Example 6

CD27L is Rapidly Internalised on Antibody Binding to Renal Cell Carcinoma-Derived Cell Lines To determine whether CD27L is a suitable target for cytotoxic-conjugated antibody therapy, an investigation of CD27L internalisation on antibody binding was performed. An anti-CD27L antibody was added to live A498 and 786-0 cells that had been cooled to minimise membrane turnover. After a 20 minute incubation at 4° C., a subgroup of the cells was fixed to represent a 0 hr time-point, and warmed serum was added to the remainder of the cells that were subsequently fixed at 1, 2, and 4 hour time-points. Evidence of internalisation of the anti-CD27L antibody-receptor complex was visualised immunocytochemically as described in Example 5. Results showed that for both the A498 and 786-0 cells at 0 hour there was clear plasma-membrane staining only with the anti-CD27L antibody. However, after 1 hour incubation there was clear internalisation of the antibody-receptor complex as evidenced by a reduction in intensity of plasma-membrane staining and appearance of antibody-containing vesicles within the cells. Internalisation was even more pronounced at 2 hours, and after 4 hours the antibody had completely internalised.

Figure 6:
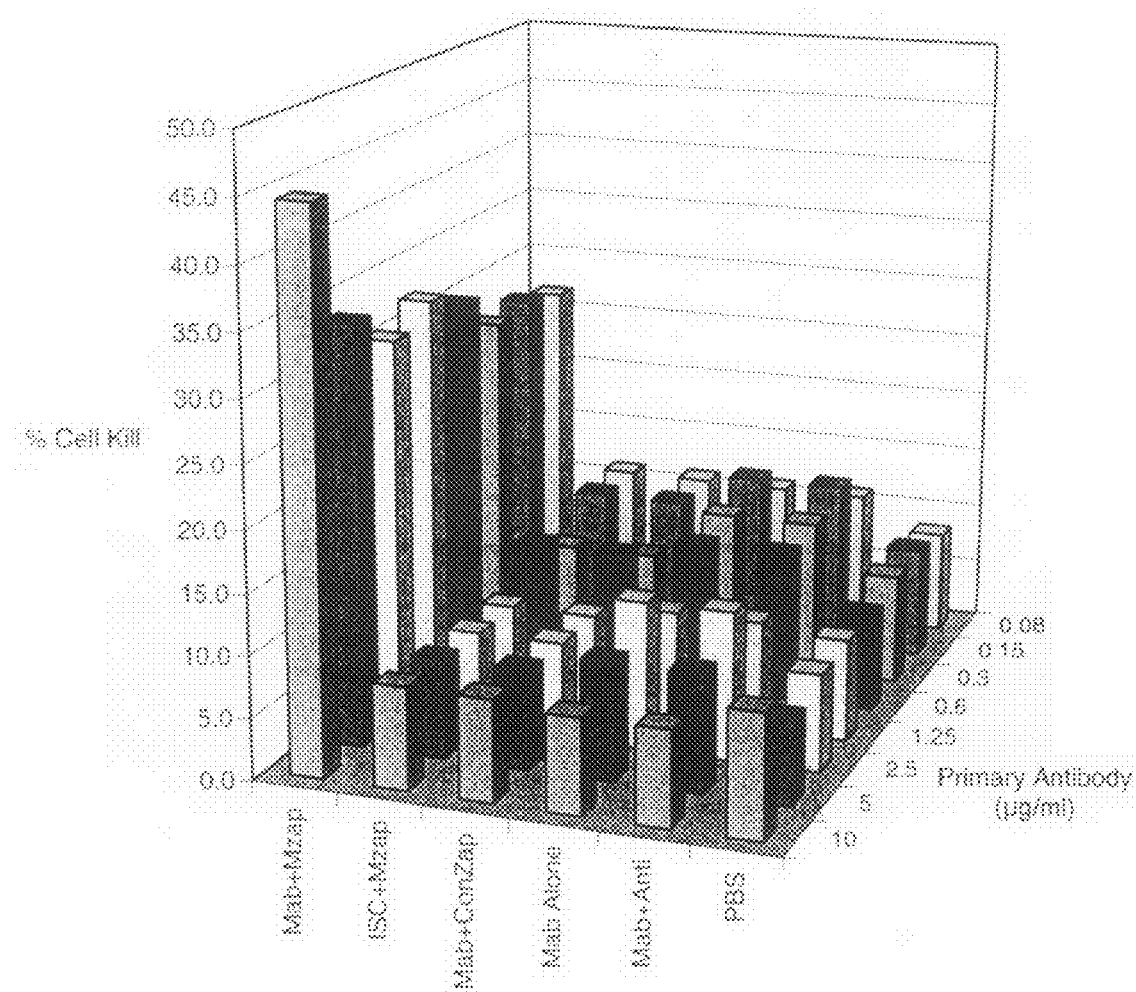
FIG. 6: shows a histogram indicating the % cell kill following incubation in a range of primary antibody concentrations. Propidium Iodide exclusion analysis was used to calculate the % cell kill. Mab=anti-CD27L, Mzap=Goat anti-mouse Saporin conjugate, ISC=IgG1 isotype control, ConZap=Saporin-conjugated Goat IgG, Anti=Goat anti-mouse IgG. Data shown is representative of three separate experiments.

To investigate the ability of an anti-CD27L antibody-receptor complex to internalise with a toxin and kill renal cell carcinoma cell lines expressing endogenous CD27L, co-incubation of anti-CD27L antibody with an anti-mouse secondary antibody that was conjugated to saporin was performed to create anti-CD27L antibody/anti-mouse secondary antibody-saporin complexes, which were subsequently added to the A498 cell line for 24 hours. The findings generated using such complexes (and potentially components thereof which did not form complexes in solution) demonstrated that incubation of A498 cells with 10 μg/ml primary antibody in the presence of 5 μg/ml saporin-conjugated secondary antibody led to approximately 45% cell death (FIG. 6). In contrast, all the appropriate control incubations resulted in approximately 5% cell death. A range of other primary antibody concentrations was used, with significant cell kill (25%) observed with 0.08 μg/ml, the lowest concentration of primary antibody tested (FIG. 6). Thus, FIG. 6 shows that targeting CD27L on A498 cells with a monoclonal antibody and Saporin-conjugated secondary antibody results in specific cell kill.

Example 7

Figure 7:
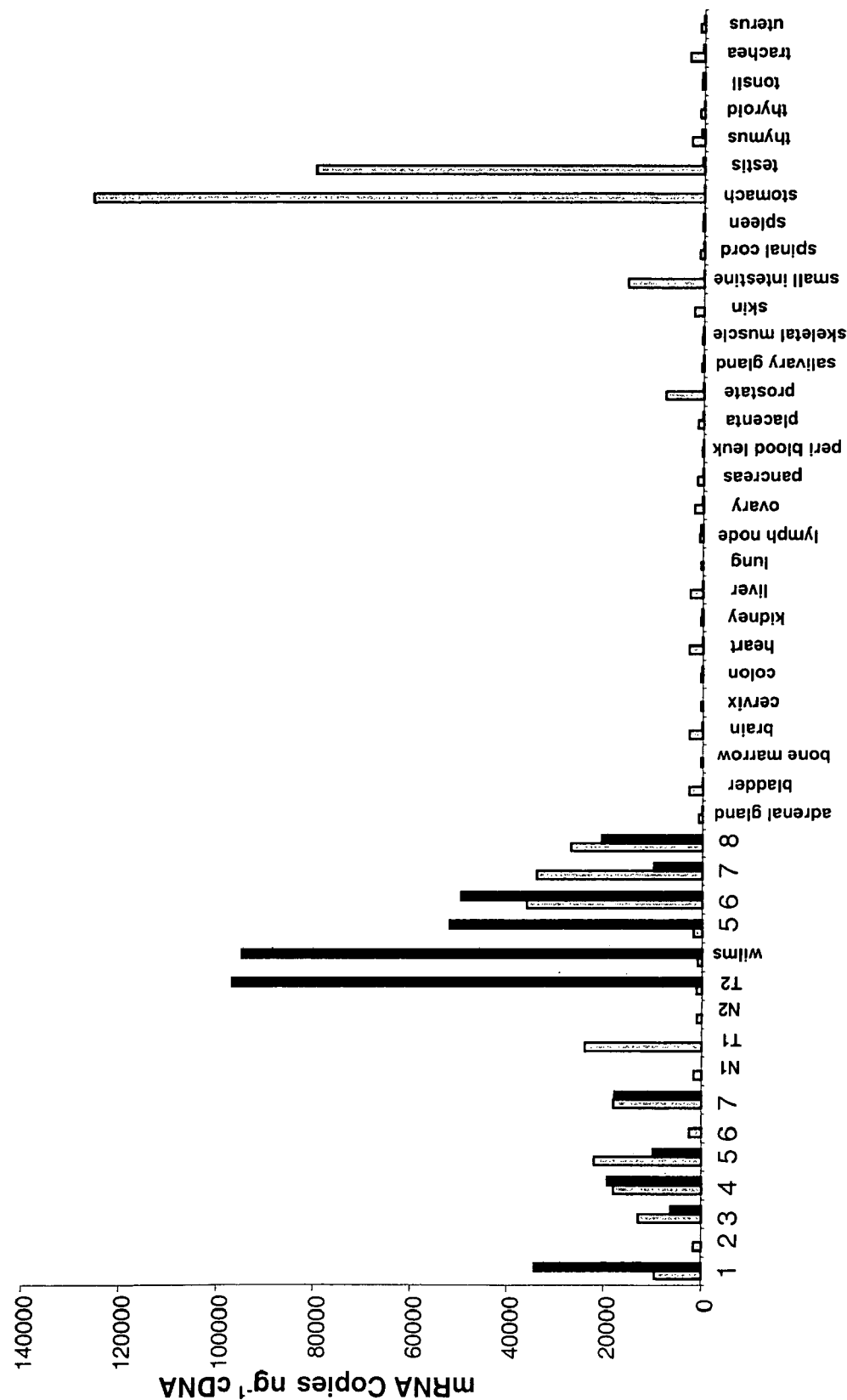
FIG. 7: compares the mRNA expression levels of CD27L (black bars) and carbonic anhydrase IX (open bars) in normal and kidney carcinoma tissues. Real-time quantitative RT-PCR analysis was used to calculate the mRNA copies per ng cDNA of CD27L and carbonic anhydrase IX in a range of 29 normal tissues, 7 kidney carcinoma donor tissues (labeled numbers 1 to 7 which are the same samples as used in FIG. 4, from Medical Solutions, plc, Nottingham, UK), 2 kidney carcinoma donors which had matched adjacent normal tissue (N=normal, T=tumour; again samples matched N1/T1 and matched N2/T2 as in FIG. 4, from Clontech), a Wilms tumour and a further 4 renal cell carcinoma donor tissues (numbers 5-8; clear cell sub-type). 1=a renal cell carcinoma containing both granular and clear cells; 2=a chromophobe renal adenocarcinoma; 3=a renal cell carcinoma having a tubular pattern with slightly oxyphilic cells; 4=unknown kidney cancer; 5=transitional cell carcinoma arising from renal pelvis; 6=unknown; 7=renal cell carcinoma of clear cell type.

CD27L Exhibits a More Restricted Normal Tissue Distribution and Higher Prevalence of Expression in Renal Cell Carcinoma Tissues than Carbonic Anhydrase IX Carbonic anhydrase IX (CA9) is a known antigen currently being targeted for renal cell carcinoma immunotherapy. Comparison of CD27L and CA9 expression was performed using real-time quantitative RT-PCR analysis on multiple normal tissues and clinical renal cell carcinoma samples (FIG. 7). These data showed that there was no detectable CD27L mRNA in any of the 29 normal tissues examined, however, there were high levels of CA9 in the stomach and testis, and to a lesser extent in the small intestine and prostate. In the clinical renal cell carcinoma samples, the overall level and prevalence of CD27L mRNA was greater than that of CA9 (FIG. 7).

In summary, CD27L was expressed specifically on approximately 80% of renal cell carcinoma clinical specimens (see Table 1; clear cell carcinoma) and expression was retained in metastatic tissues from primary renal cell carcinoma (see Example 5). In addition, it has been demonstrated that binding of an anti-CD27L antibody to cell lines endogenously expressing CD27L results in the rapid internalisation of the antibody-receptor complex (Example 6). These data therefore describe the identification of an antigen that is highly expressed on renal cell carcinoma tissues but has a very restricted normal tissue expression making it an ideal target as a diagnostic and/or for the treatment of renal cell carcinomas using cytotoxic immunotherapy.

While certain embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method of screening for and/or diagnosis of epithelial-derived cancer in a subject, and/or monitoring the effectiveness of epithelial-derived cancer therapy, which comprises the step of detecting and/or quantifying in a biological sample obtained from said subject, a CD27L polypeptide which comprises or consists of the amino acid sequence of SEQ ID NO: 2.

2. The method of claim 1, wherein the level of said polypeptide is compared to a previously determined reference range or control.

3. The method according to claim 1, wherein the step of detecting comprises:
    (a) contacting the sample with a capture reagent that is specific for a polypeptide as defined in claim 1; and
    (b) detecting whether binding has occurred between the capture reagent and said polypeptide in the sample.

4. The method according to claim 3, wherein step (b) comprises detecting the captured polypeptide using a directly or indirectly labelled detection reagent.

5. The method according to claim 3, wherein the capture reagent is immobilised on a solid phase.

6. The method according to claim 1, wherein the polypeptide is detected and/or quantified using an antibody that specifically binds to one or more CD27L polypeptides as defined in claim 1.

7. A method of screening for anti-epithelial-derived cancer agents that interact with a CD27L polypeptide as defined in claim 1, said method comprising:
    (a) contacting said polypeptide with a candidate agent; and
    (b) determining whether or not the candidate agent interacts with said polypeptide.

8. The method according to claim 7, wherein the determination of interaction between the candidate agent and CD27L polypeptide comprises quantitatively detecting binding of the candidate agent and said polypeptide.

9. A method of screening for anti-epithelial-derived cancer agents that modulate
    (a) the expression or activity of a CD27L polypeptide as defined in claim 1, comprising
        (i) comparing the expression or activity of said polypeptide in the presence of a candidate agent with the expression or activity of said polypeptide in the absence of the candidate agent or in the presence of a control agent; and
        (ii) determining whether the candidate agent causes the expression or activity of said polypeptide to change.

10. The method of claim 9, wherein the expression or activity level of said polypeptide is compared with a predetermined reference range.

11. The method of claim 9, which additionally comprises selecting an agent which modulates the expression or activity of said polypeptide for further testing, or therapeutic or prophylactic use as an anti-epithelial-derived cancer agent.

12. The method of claim 1, wherein the epithelial-derived cancer is selected from colorectal cancer and kidney cancer.

13. The method of claim 7, wherein the epithelial-derived cancer is selected from colorectal cancer and kidney cancer.

14. The method of claim 9, wherein the epithelial-derived cancer is selected from colorectal cancer and kidney cancer.

15. The method of claim 12, wherein the kidney cancer is renal cell carcinoma of the clear cell type.

16. The method of claim 13, wherein the kidney cancer is renal cell carcinoma of the clear cell type.

17. The method of claim 14, wherein the kidney cancer is renal cell carcinoma of the clear cell type.

* * * * *